(12) United States Patent
Isoda et al.

(10) Patent No.: US 10,085,624 B2
(45) Date of Patent: Oct. 2, 2018

(54) MANIPULATOR AND MANIPULATOR SYSTEM

(71) Applicant: OLYMPUS CORPORATION, Tokyo (JP)

(72) Inventors: Takumi Isoda, Tokyo (JP); Naoya Hatakeyama, Tokyo (JP); Masatoshi Iida, Tokyo (JP); Sadahiro Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 99 days.

(21) Appl. No.: 15/006,422

(22) Filed: Jan. 26, 2016

(65) Prior Publication Data
US 2016/0135663 A1 May 19, 2016

Related U.S. Application Data

(63) Continuation of application No. PCT/JP2014/067792, filed on Jul. 3, 2014.

(30) Foreign Application Priority Data

Jul. 26, 2013 (JP) ................................ 2013-155480

(51) Int. Cl.
*A61B 1/005* (2006.01)
*A61B 1/04* (2006.01)
(Continued)

(52) U.S. Cl.
CPC ........ *A61B 1/0057* (2013.01); *A61B 1/00045* (2013.01); *A61B 1/0052* (2013.01);
(Continued)

(58) Field of Classification Search
CPC ... A61B 1/0057; A61B 1/00045; A61B 1/018; A61B 1/04; A61B 1/06; A61B 1/0006;
(Continued)

(56) References Cited

U.S. PATENT DOCUMENTS 6,013,024 A * 1/2000 Mitsuda ............. A61B 1/00039
600/146
2005/0168571 A1 8/2005 Lia et al.
(Continued)

FOREIGN PATENT DOCUMENTS

CN 102188220 A 9/2011
CN 102711582 A 10/2012
(Continued)

OTHER PUBLICATIONS

International Search Report dated Oct. 7, 2014 issued in PCT/JP2014/067792.
Extended Supplementary European Search Report dated Mar. 9, 2017 in European Patent Application No. 14 83 0091.6.

*Primary Examiner* — Timothy J Neal
(74) *Attorney, Agent, or Firm* — Scully, Scott, Murphy & Presser, P.C.

(57) ABSTRACT

The invention has for its object to provide a manipulator and manipulator system in which a dynamic surplus is rapidly removed and a moving assembly actuates rapidly in association with the operation of an operating assembly.

The manipulator 1 includes an operating assembly 2 operated by an operator, a moving assembly 3 operated by the operating assembly 2, a transmitting assembly 4 for coupling the operating assembly 2 to the moving assembly 3 to transmit driving force of the operating assembly 2 to the moving assembly 3, and a transmission compensating assembly 6 for making up for a dynamic surplus occurring in the transmitting assembly 4 in association with the operation of the operating assembly 2.

17 Claims, 20 Drawing Sheets

(51) Int. Cl.
*A61B 1/00* (2006.01)
*B25J 3/04* (2006.01)
*B25J 9/16* (2006.01)
*A61B 1/06* (2006.01)
*A61B 34/00* (2016.01)
*A61B 1/018* (2006.01)

(52) U.S. Cl.
CPC .................. *A61B 1/04* (2013.01); *A61B 1/06* (2013.01); *A61B 34/70* (2016.02); *A61B 34/71* (2016.02); *B25J 3/04* (2013.01); *B25J 9/1689* (2013.01); *A61B 1/00006* (2013.01); *A61B 1/018* (2013.01); *A61B 2034/715* (2016.02); *G05B 2219/35417* (2013.01); *G05B 2219/39439* (2013.01); *G05B 2219/45118* (2013.01); *G05B 2219/49253* (2013.01)

(58) Field of Classification Search
CPC ....... A61B 1/0052; A61B 34/70; A61B 34/71; A61B 1/005; B25J 3/04; B25J 9/1689
See application file for complete search history.

(56) References Cited

U.S. PATENT DOCUMENTS

| | | |
|---|---|---|
| 2008/0139886 A1 | 6/2008 | Tatsuyama |
| 2011/0295063 A1* | 12/2011 | Umemoto ............. A61B 1/008 600/109 |
| 2012/0046522 A1* | 2/2012 | Naito .................. A61B 1/00006 600/118 |
| 2012/0220832 A1 | 8/2012 | Nakade et al. |
| 2013/0144275 A1 | 6/2013 | Umemoto |

FOREIGN PATENT DOCUMENTS

| | | |
|---|---|---|
| EP | 2 599 431 A1 | 6/2013 |
| JP | S50-025083 A | 3/1975 |
| JP | H03-292928 A | 12/1991 |
| JP | H06-189897 A | 7/1994 |
| JP | H10-217167 A | 8/1998 |
| JP | 2000-300511 A | 10/2000 |
| JP | 2005-013320 A | 1/2005 |
| JP | 2009-090087 A | 4/2009 |
| JP | 2009-201607 A | 9/2009 |
| JP | 5048158 B2 | 10/2012 |
| WO | WO 2011/108161 A1 | 9/2011 |

\* cited by examiner

FIG.1
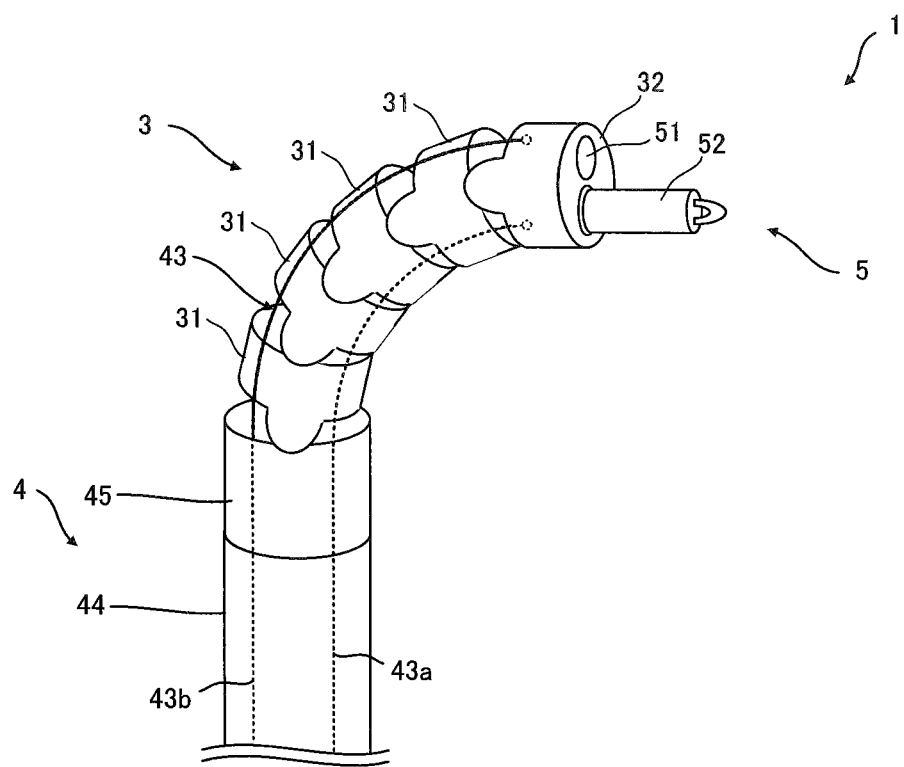
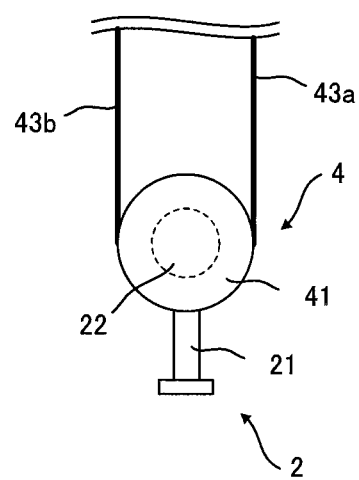

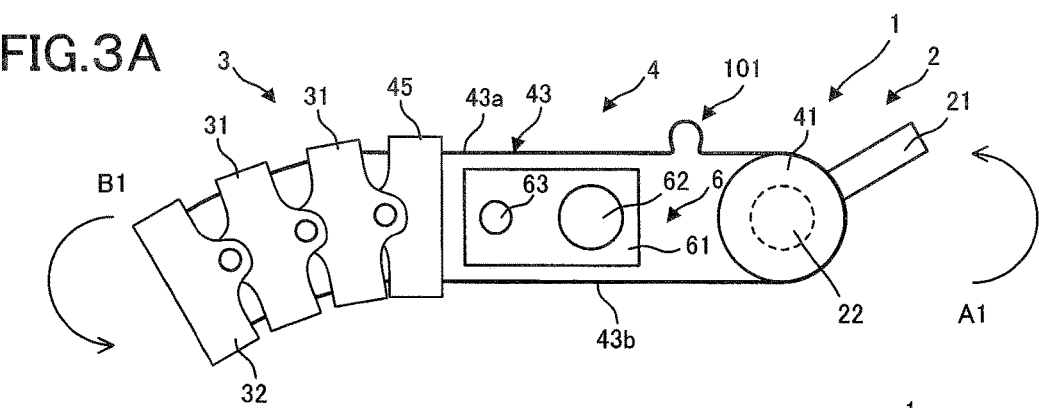
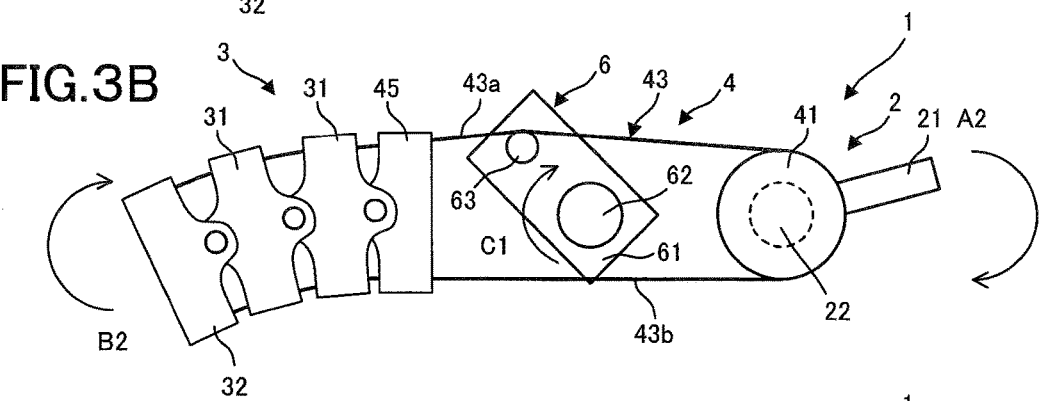
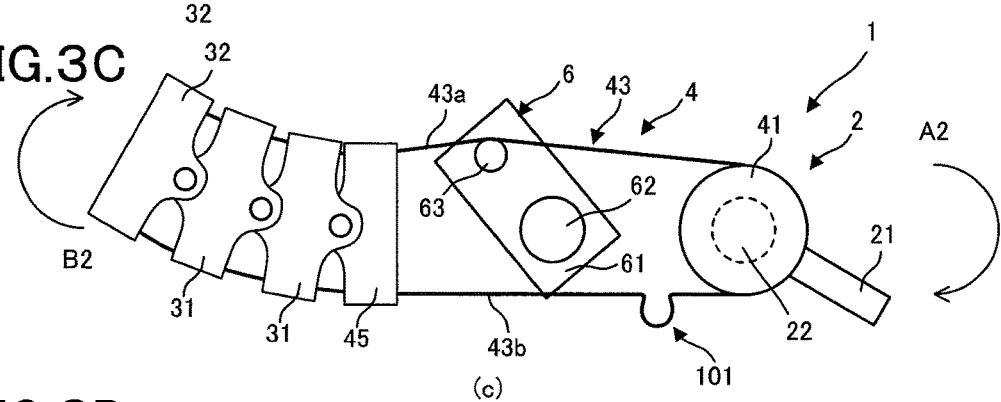
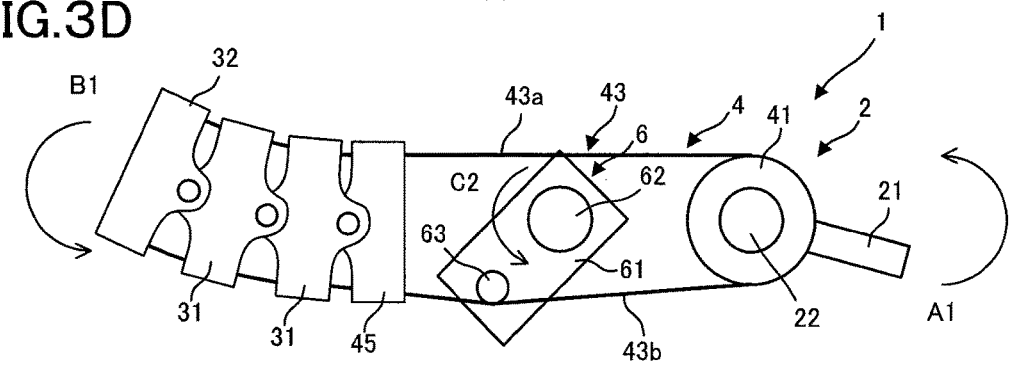

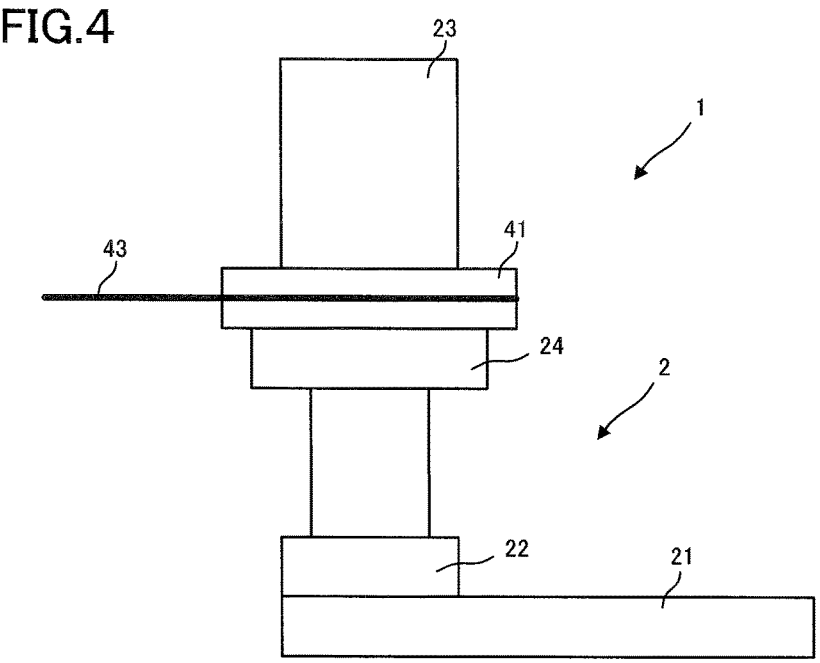

(a)

MANIPULATOR AND MANIPULATOR SYSTEM

CROSS-REFERENCE TO RELATED APPLICATIONS

This application is a continuation claiming priority on the basis of Japan Patent Application No. 2013-155480 applied in Japan on Jul. 26, 2013 and based on PCT/JP2014/067792 filed on Jul. 3, 2014. The contents of both the PCT application and the Japan Application are incorporated herein by reference.

BACKGROUND OF THE INVENTION AND RELATED ART STATEMENT

The present invention relates to a manipulator and a manipulator system, each having an operating assembly mechanically connected to a moving assembly.

So far there has been a manipulator disclosed in Patent Publication 1, wherein one end of a wire inserted through a hollow shaft is routed around a driving pulley and the other end is done around a driven pulley for power transmission.

With the manipulator disclosed in JP(A) 2009-201607, however, there is no power transmission ensured when no sufficient tension is applied to the wire routed around and between the driving pulley and the driven pulley. It is thus required to adjust the tension of the wire for rapid and precise power transmission.

FIG. 20 is illustrative in schematic of a conventional manipulator.

As shown in FIG. 20(a), a wire 140 routed around and between an operating-side pulley 122 and a moving-side pulley 132 of a manipulator 110 in a neutral state has often a small slack 100. The manipulator of Patent Publication 1 is previously cleared of such a small wire slack by adjustment of the wire tension.

On the other hand, such as when an operator (not shown) rotates a handle 121 from a neutral state of FIG. 20A in a direction indicated by an arrow A1, there are possible elongation of a wire 141 and friction or the like due to contact of a wire 140 with a guide member that receives the wire 140 in association with rotation of the handle 121 and operating-side pulley 122 in the direction indicated by the arrow A1, resulting in a dynamic slack 101 as shown in FIG. 20B.

Thereafter, when the handle 121 is reversed in a direction indicated by an arrow A2 as shown in FIGS. 20B through 20C, there is no tensile force transmitted to the moving-side pulley 132 until the dynamic slack 101 shown in FIG. 20B is taken out of the wire 140 with the result that the moving member 131 is unlikely to be actuated even with the operation of the handle 121 as shown in FIG. 20C.

SUMMARY OF THE INVENTION

The manipulator according to one embodiment of the invention includes
 an operating assembly operated by an operator;
 a moving assembly operated by the operating assembly;
 a transmitting assembly that couples the operating assembly to the moving assembly to transmit a driving force of the operating assembly to the moving assembly; and
 a transmission compensating assembly that makes up for a dynamic surplus occurring in the transmitting assembly in association with operation of the operating assembly.

BRIEF EXPLANATION OF THE DRAWINGS

FIG. 1 shows one example of the manipulator according to the invention.

FIGS. 3A-3D are illustrative in schematic of the actuation of the first example of the manipulator according to the first embodiment of the invention.

FIG. 4 is illustrative in schematic of the second example of the manipulator according to the first embodiment of the invention.

DETAILED DESCRIPTION OF EMBODIMENTS

Figure 2:
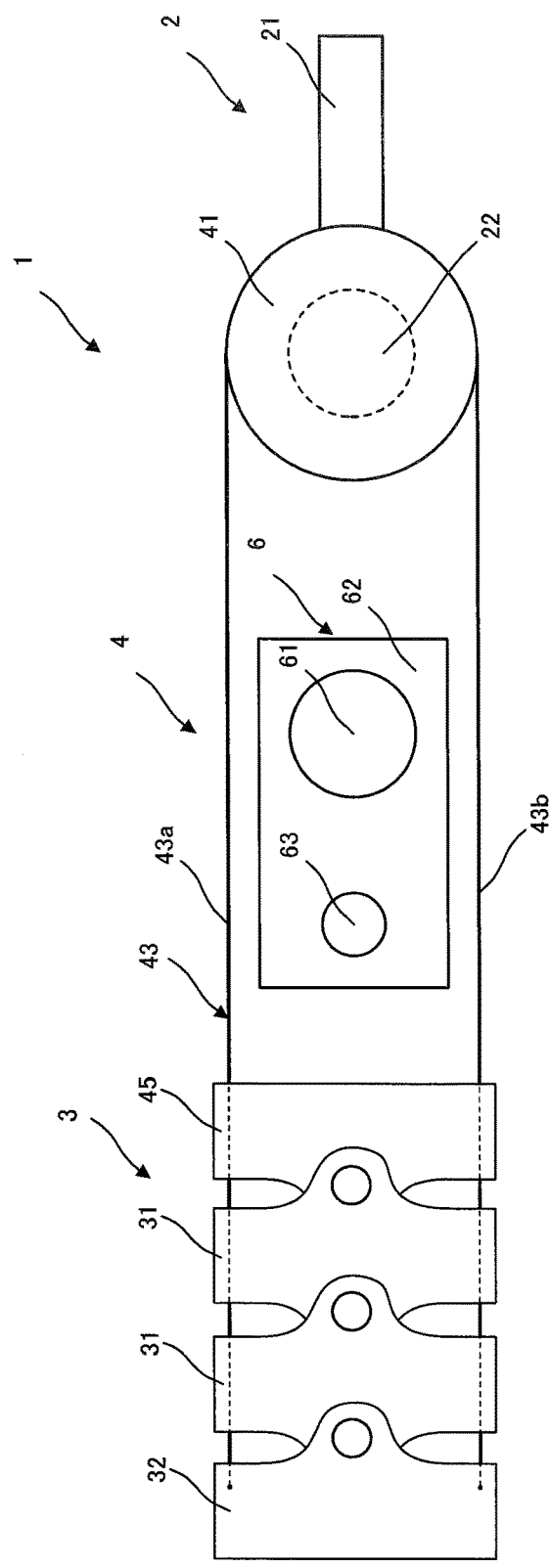
FIG. 2 is illustrative in schematic of the first example of the manipulator according to the first embodiment of the invention.

One embodiment of the invention will now be explained.

FIG. 1 shows on example of the manipulator 1 according to one embodiment of the invention.

As illustrated in FIG. 1, the manipulator 1 described here comprises an operating assembly 2, a moving assembly 3, a transmitting assembly 4, and a treatment assembly 5. The operating assembly 2 is mechanically connected to the moving assembly 3 through the transmitting assembly 4. As an operator operates the operating assembly 2 in action, it causes operating force to be transmitted to the moving assembly 3 via the transmitting assembly 4 for movement of the moving assembly 3.

The operating assembly 2 comprises a handle 21 and a first encoder 22. In the embodiment described here, the handle 21 is schematically shown in the form of a rod member, but it may take the form of a multi-joint arm or a member having a shape suitable for operating a treatment tool or the like disposed on the moving assembly 3 such as the grips of scissors. The encoder 22 is provided to acquire the angle of the handle 21.

The moving assembly 3 includes a plurality of bending tops 31 and a rigid distal-end portion 32. The moving assembly 3 comprises a plurality of substantially ring-like bending tops 31 arranged axially side-by-side with the rigid distal-end portion 32 disposed at the distal end. The adjoining bending tops 31 are rotatable in relation to each other, and the bending tops 31 adjacent to the rigid distal-end portion 32 is rotatable too. The rigid distal-end portion 32 may optionally be provided with an endoscope 51 or the like as the treatment assembly 5.

The transmitting assembly 4 includes an operating-side pulley 41, a transmitting wire 43, a flexible portion 44, and a transition portion 45.

The operating-side pulley 41 is connected to the handle 21 in the operating assembly 2, and rotates based on the operation of the handle 21. The transmitting wire bundle 43 includes a first transmitting wire 43a and a second transmitting wire 43b fixed at the respective distal ends to the rigid distal-end portion 32 and at the respective other ends to the handle 21. As the rigid distal-end portion 32 moves on the basis of the operation of the handle 21, it causes movement of the moving assembly 3. The flexible portion 44 covers at least a portion of the transmitting wire 43, and is formed of a bendable, flexible tubular member. The transition portion 45 is located on the side of the flexible portion 44 facing the moving assembly 3. The transition portion 45 is rotatably mounted with one end bending tops 31 of multiple bending tops 31 in the moving assembly 3. Note here that the transmitting assembly 4 may have a pulley on the moving assembly side.

The treatment assembly 5 includes an endoscope 51 and a treatment tool 52, and is located within the rigid distal-end portion 32. The endoscope 51 includes a viewing optical system and a lighting optical system.

Through such structure, the manipulator 1 described here is actuated as follows. As the operator operates the handle 21 in the operating assembly 2, it causes the operating-side pulley 41 to rotate and a portion of the transmitting wire 43 routed around the operating-side pulley 41 to be towed thereby pulling one of the rigid distal-end portions 32 and slackening the other. As the rigid distal-end portion 32 is pulled, it causes the bending tops 31 to rotate, resulting in a bending of the moving assembly 3.

FIG. 2 is illustrative in schematic of the first example of the manipulator 1 according to the first embodiment of the invention, and FIGS. 3A-3D are illustrative in schematic of the actuation of the first example of the manipulator 1 according to the first embodiment of the invention.

The first example of the manipulator 1 according to the first embodiment of the invention comprises an operating assembly 2, a moving assembly 3, a transmitting assembly 4, and a transmission compensating assembly 6. The operating assembly 2, moving assembly 3, and transmitting assembly 4 may be constructed in the same way as explained with reference to FIG. 1.

The transmission compensating assembly 6 includes a compensating motor 61, a moving member 62, and an urging member 63. The compensating motor 61 comprises an actuator such as a motor to move the moving member 62 and urging member 63. The urging member 63 is supported on the moving member 62, and rotates together with the moving member 62 to urge the transmitting wire 43 in the transmitting assembly 4.

The first example of the manipulator 1 according to the first embodiment of the invention is actuated as follow.

When an operator (not shown) rotates the handle 21 from a neutral state shown in FIG. 2 in a direction indicated by an arrow A1 as shown in FIG. 3A, a dynamic slack 101 that provides dynamic surplus is produced in association with the rotation of the handle 21 and operating-side pulley 41 in the direction of arrow A1.

Thereafter, when the handle 21 is reversed from the direction of arrow A1 back in a direction indicated by an arrow A2 as shown in FIGS. 3A and 3B, the first encoder 22 detects the reversal of the handle 21. Upon detection of the reversal of the handle 21 by the first encoder 22, the compensating motor 61 in the transmission compensating assembly 6 is driven to rotate the urging member 63 in a direction indicated by an arrow C1 as shown in FIG. 3B.

As shown in FIG. 3B, the urging member 63 urges the first transmitting wire 43a in the transmitting assembly 4 so that a dynamic slack 101 in the first transmitting wire 43a shown in FIG. 3A can rapidly be removed. Removal of the dynamic slack 101 causes the tensile force of the first transmitting wire 43a to be rapidly transmitted to the moving assembly 3 for its rotation in a direction indicated by an arrow B2.

Further, rotation of the handle 21 in the direction of arrow A2 causes the dynamic slack 101 to be produced in the second transmitting wire 43b on the side into which the handle 21 rotates.

Thereafter, when the handle 21 is reversed from the direction of arrow A1 back to the direction of arrow A2 as shown in FIGS. 3C through 3D, the first encoder 22 detects the reversal of the handle 21. Upon detection of the reversal of the handle 21 by the first encoder 22, the compensating motor 61 in the transmission compensating assembly 6 is driven to rotate the urging member 63 in the direction indicated by an arrow C2, as shown in FIG. 3D.

As the urging member 63 urges the second transmitting wire 43b in the transmitting assembly 4 as illustrated in FIG. 3D, it causes rapid removal of the dynamic slack 101 in the second transmitting wire 43b depicted in FIG. 3C. Upon removal of the dynamic slack 101, the tensile force of the second transmitting wire 43b occurring from the rotation of the handle 21 is rapidly transmitted to the moving assembly 3 for rotation in the direction of arrow B1.

According to the first example of the manipulator 1, it is thus possible to rapidly take the dynamic slack 101 out of the transmitting wire 43 and, hence, rotate the moving assembly 3 rapidly in association with the rotation of the handle 21.

FIG. 4 is illustrative in schematic of the second example of the manipulator 1 according to the first embodiment of the invention.

Referring to such manipulator 1 as represented by the first example of FIG. 2, the transmitting wire 43 is pulled upon removal of the dynamic slack 101 by the transmission compensating assembly 6. This in turn gives rise to a slight counteraction that may possibly be transmitted from the transmitting wire 43 to the hand taking a grip of the handle 21 in the operating assembly 2.

Referring here to the second example of the manipulator 1 according to the first embodiment of the invention, the first example of the manipulator 1 further includes a torque generator 23 or a decelerator 24 in the operating assembly 2. The rest of the manipulator 1 may be the same as explained with reference to FIG. 1; so they will not be explained any more.

The torque generator 23 is provided to make the counteraction from the transmitting wire 43 upon removal of the dynamic slack 101 less likely to be transmitted to the hand. For instance, when a motor is used as the torque generator 23, the counteraction from the transmitting wire 43 is not transmitted to the hand unless the motor is rotated by the tensile force of the transmitting wire 43. Actually, the counteraction from the transmitting wire 43 is not strong enough to rotate the motor, so that it is not transmitted to the hand taking a grip of the handle 21.

When a motor is used as the torque generator 23, it may be driven to rotate the operating-side pulley 41 for removal of slacks in the transmitting wire 43 or rotate the operating-side pulley 41 to assist in the operating force of rotation of the handle 21 with the result that it can be operated with agility.

The decelerator 24 is provided to decelerate the rotation of the operating-side pulley 41 for transmission to the handle 21. In turn, this makes the amount of rotation of the handle 21 in association with the rotation of the operating-side pulley 41 smaller so that the movement of the transmitting wire 43 upon removal of the dynamic slack 101 is hardly transmitted to the handle 21.

Figure 5A:
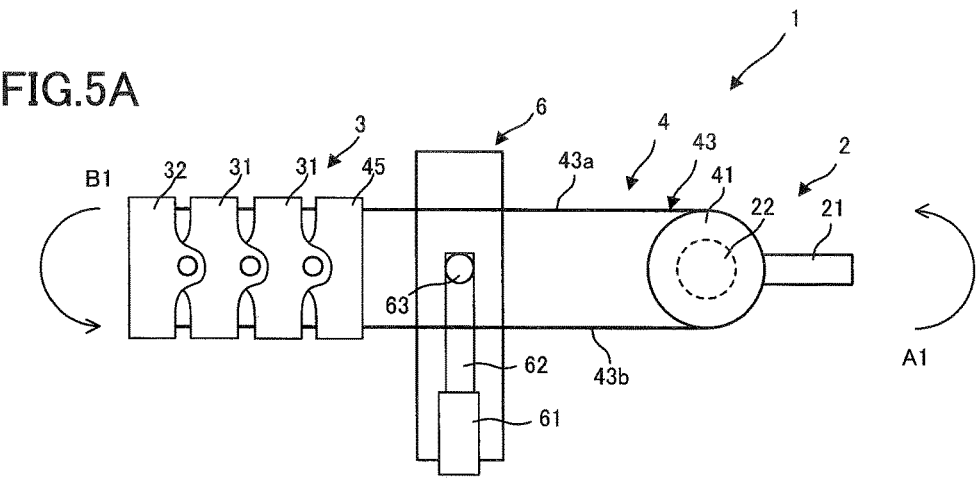
FIGS. 5A-5C are illustrative in schematic of the third example of the manipulator according to the first embodiment of the invention.
Figure 5B:
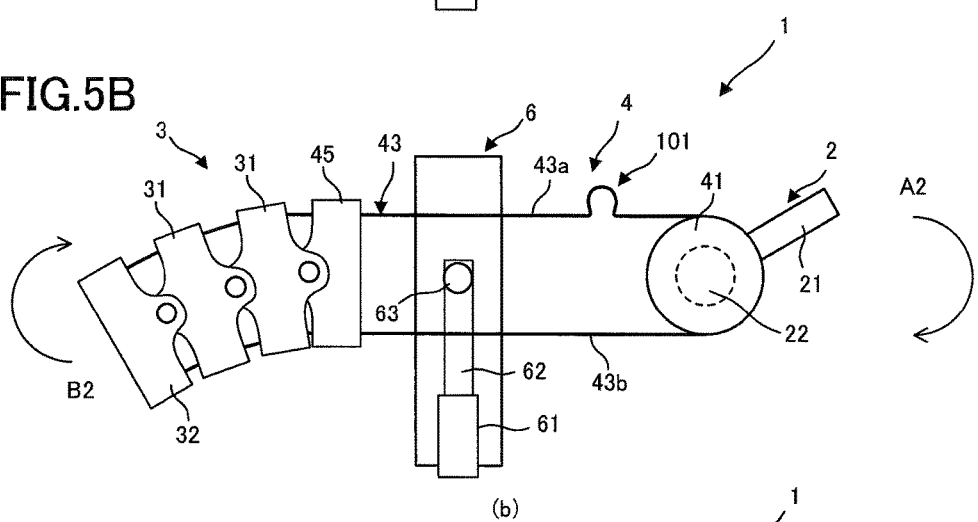
Figure 5C:
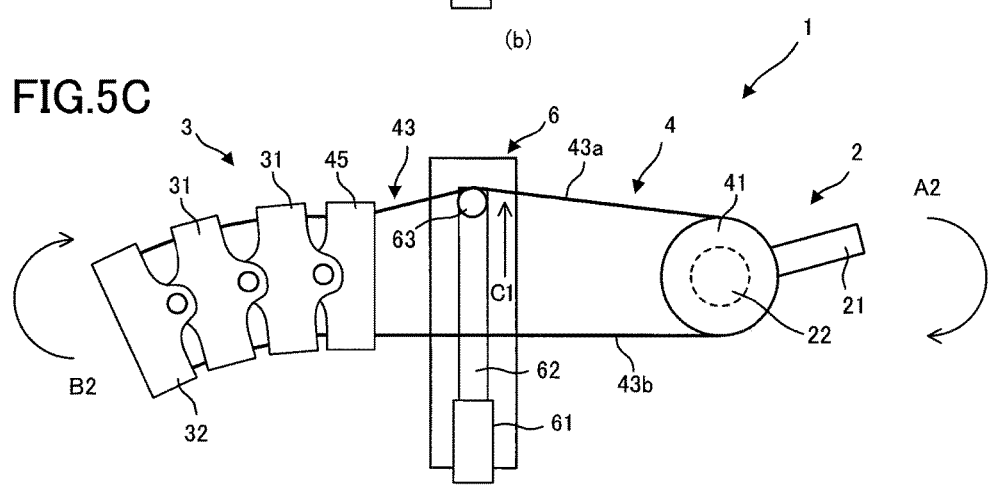

FIGS. 5A-5C are illustrative in schematic of the third example of the manipulator 1 according to the first embodiment of the invention.

Referring to the third example of the manipulator 1 shown in FIGS. 5A-5C, the transmission compensating assembly 6 of the first example of the manipulator 1 is partly modified in construction. The rest of the manipulator may be the same as explained with reference to FIG. 1; so they will not be explained any more.

In the third example described here, the transmission compensating assembly 6 includes a compensating motor 61, a moving member 62, and an urging member 63. The compensating motor 61 comprises an actuator such as a motor to move the urging member 63. The urging member 63 is supported on the moving member 62, and moves together with the moving member 62 to urge the transmitting wire 43 in the transmitting assembly 4.

The third example of the manipulator 1 according to the first embodiment of the invention is actuated as follows.

When an operator (not shown) rotates the handle 21 from a neutral state depicted in FIG. 5A in the direction of arrow A1 into a state of FIG. 5B, there is a dynamic slack 101 occurring in association with the rotation of the handle 21 and operating-side pulley 41 in the direction of arrow A1, as shown in FIG. 5B.

Thereafter, when the handle 21 is reversed from the direction of arrow A1 back to the direction of arrow A2 as depicted in FIGS. 5B and 5C, the first encoder 22 detects the reversal of the handle 21. Upon detection of the reversal of the handle 21 by the first encoder 22, the compensating motor 61 in the transmission compensating assembly 6 is driven to move the urging member 63 in the direction of arrow C1 as illustrated in FIG. 5C.

Referring to the third example of the manipulator 1, as the urging member 63 urges the first transmitting wire 43a as illustrated in FIG. 5C, it causes rapid removal of the dynamic slack 101 in the first transmitting wire 43a depicted in FIG. 5B. Upon removal of the dynamic slack 101, the tensile force of the first transmitting wire 43a occurring from the rotation of the handle 21 is rapidly transmitted to the moving assembly 3 for rotation in the direction of arrow B2.

According to the third example of the manipulator 1, it is thus possible to effect rapid removal of the dynamic slack 101 in the transmitting wire 43 and make sure rapid rotation of the moving assembly 3 in association with the rotation of the handle 21. The third example of the manipulator 1 may be installed in a smaller space or footprint as compared with the first example because there is a shorter moving distance of the urging member 63 until the transmitting wire 43 is urged.

Figure 6A:
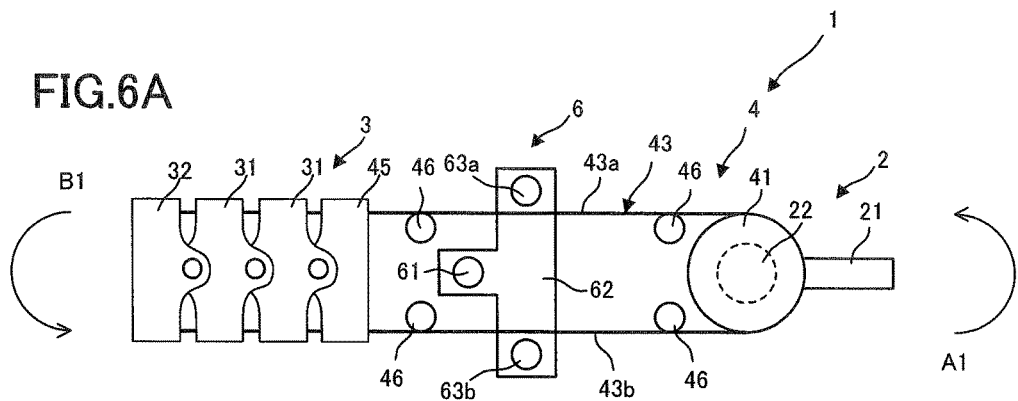
FIGS. 6A-6C are illustrative in schematic of the fourth example of the manipulator according to the first embodiment of the invention.
Figure 6B:
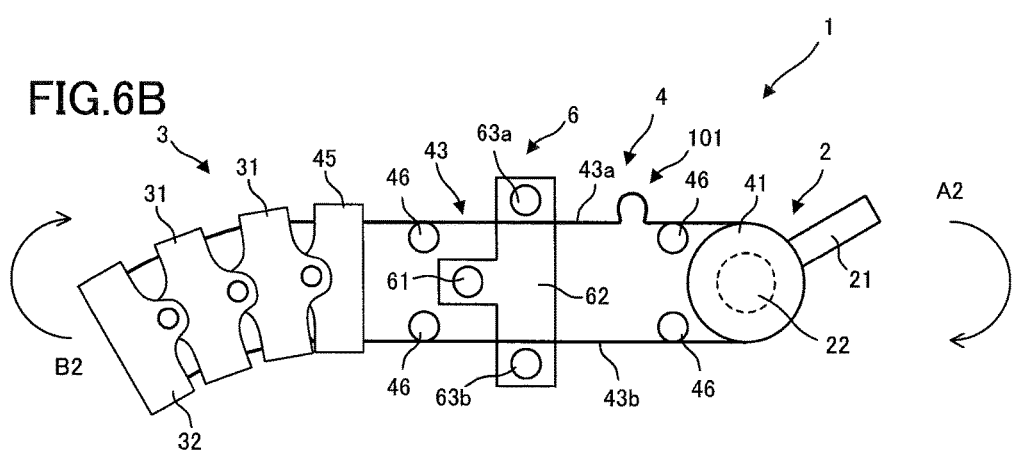
Figure 6C:
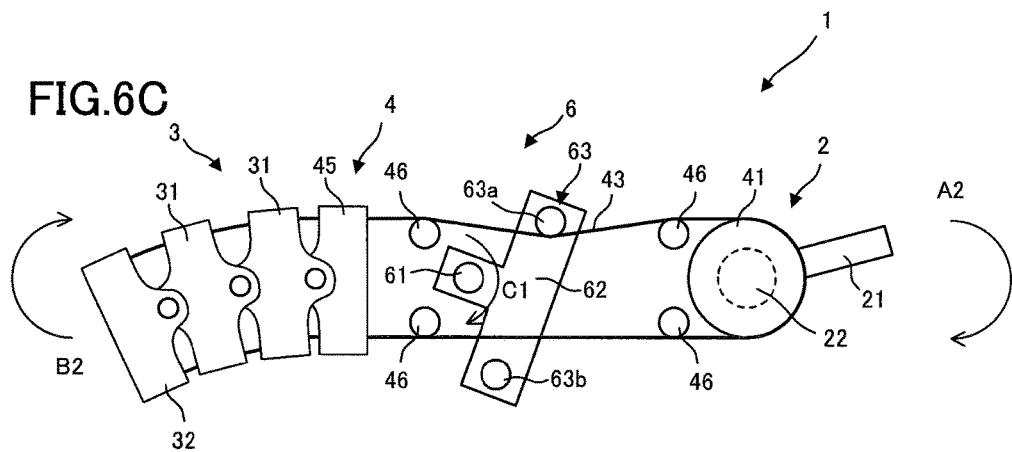

FIGS. 6A-6C are illustrative in schematic of the fourth example of the manipulator 1 according to the first embodiment described herein.

Referring to the fourth example of the manipulator 1 shown in FIGS. 6A-6C, the transmitting assembly 4 and transmission compensating assembly 6 of the first example of the manipulator 1 are partly modified in construction. The rest of the manipulator may be the same as explained with reference to FIG. 1; so they will not be explained any more.

In the fourth example, the transmission compensating assembly 6 includes a compensating motor 61, a moving member 62, and an urging member 63. The urging member 63 comprises a first urging member 63a and a second urging member 63b. In the fourth example, the transmitting assembly 4 includes guide rollers 46 in addition to the configuration of the transmitting assembly 4 in the first example.

In a neutral state as shown in FIG. 6A, the moving member 62 supports the first 63a and the second urging member 63b in opposite positions outside of the transmitting wire 43. The first 63a and the second urging member 63b are supported on both end portions protruding outwardly from the transmitting wire 43, and rotate together with the moving member 62 to urge the transmitting wire 43 in the transmitting assembly 4. The moving distance of the first 63a and the second urging member 63b until they rotate to urge the transmitting wire 43 is shorter than that in the first to third examples of the manipulator 1.

The guide rollers 46 are each located inside of the transmitting wire 43 with positions in between, in which the first 63a and the second urging member 63b urge the transmitting wire 43.

The fourth example of the manipulator 1 according to the first embodiment of the invention is actuated as follows.

When an operator (not shown) rotates the handle 21 from a neutral state depicted in FIG. 6A in the direction of arrow A1 into a state of FIG. 6B, there is a dynamic slack 101 occurring as shown in FIG. 6B.

Thereafter, when the handle 21 is reversed from the direction of arrow A1 back to the direction of arrow A2 as depicted in FIGS. 6B and 6C, the first encoder 22 detects the reversal of the handle 21. Upon detection of the reversal of the handle 21 by the first encoder 22, the compensating motor 61 in the transmission compensating assembly 6 is driven to move the moving member 62 and urging member 63 in the direction of arrow C1 as illustrated in FIG. 6C.

Referring to the fourth example of the manipulator 1, as the first transmitting wire 43a is urged against the first urging member 63a between the guide rollers 46 as shown in FIG. 6C, it causes rapid removal of the dynamic slack 101 in the first transmitting wire 43a depicted in FIG. 6B. Upon removal of the dynamic slack 101, the tensile force of the first transmitting wire 43a occurring from the rotation of the handle 21 is rapidly transmitted to the moving assembly 3 for rotation in the direction of arrow B2.

According to the fourth example of the manipulator 1, it is thus possible to effect rapid removal of the dynamic slack 101 in the transmitting wire 43 and make sure rapid rotation of the moving assembly 3 in association with the rotation of the handle 21. The fourth example of the manipulator 1 makes sure rapider rotation of the moving assembly 3 in association with the rotation of the handle 21 because the moving distance of the urging member 63 until the transmitting wire 43 is urged in place is shorter than that in the first to third examples of the manipulator 1. The urging member 63 urges the transmitting wire 43 guided by the guide rollers 46 in a precise position so that there is no or little damage to the transmitting wire 43.

FIGS. 7A-7D are illustrative in schematic of the fifth example of the manipulator 1 according to the first embodiment described here.

Referring to the fifth example of the manipulator 1 shown in FIGS. 7A-7D, the transmitting assembly 4 in the fourth example of the manipulator 1 is partly modified with the addition of a surplus absorber assembly 7. The rest of the manipulator 1 may be the same as explained with reference to the fourth example of FIGS. 6A-6C; so they will not explained any more.

Referring to the transmitting assembly 4 in the fifth example, the guide rollers 46 in the transmitting assembly 4 in the fourth example are used as first guide rollers 46a, and second guide rollers 46b are located outside of the transmitting wire 43 and each of the second guide rollers 46b is opposite to each of the first guide rollers 46a with the transmitting wire 43 in between.

The surplus absorber assembly 7 includes an idler pulley 71, a resilient member 72, and a stopper 73. One idler pulley 71 is located near the first urging member 63a, and another one is disposed near the second urging member 63b. In the fifth example, the idler pulleys 71 are located inside of the transmitting wire 43, and supported by the resilient members 72 that bias and urge the transmitting wire 43 outwardly. The stopper 73 is provided to prevent the idler pulleys 71 and transmitting wire 43 from being urged inwardly from their initial positions. In the fifth example, the stopper 73 is in abutment against the idler pulleys 71 in positions where they are not biased by the resilient members 72 in a neutral state depicted in FIG. 7(a); in other words, the idler pulleys 71 are located such that they are sandwiched between the transmitting wire 43 and the stoppers 73.

The fifth example of the manipulator 1 according to the first embodiment described herein is actuated as follows.

Figure 7A:
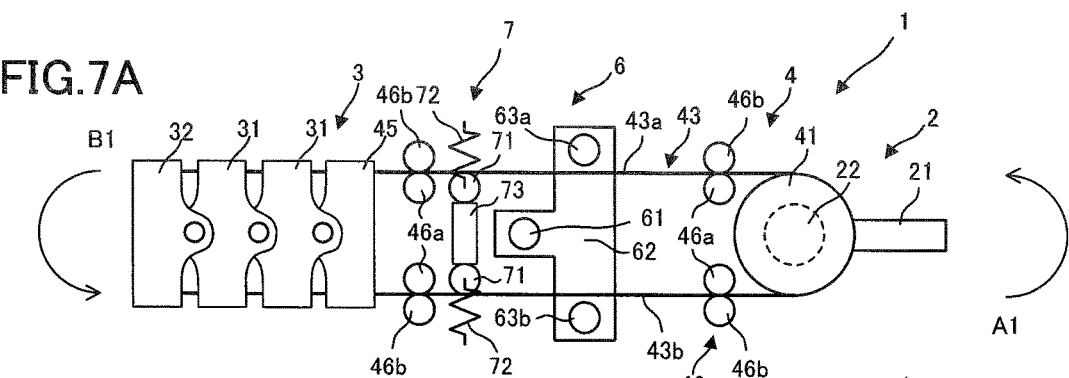
FIGS. 7A-7D are illustrative in schematic of the fifth example of the manipulator according to the first embodiment of the invention.
Figure 7B:
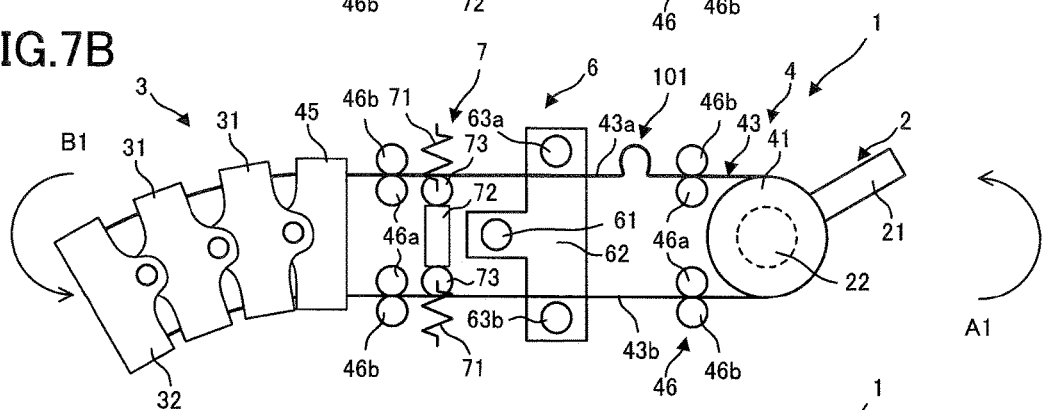

When an operator (not shown) rotates the handle 21 from a neutral state depicted in FIG. 7A in the direction of arrow A1 into a state of FIG. 7B, there is a dynamic slack 101 occurring in association with the rotation of the handle 21 and operating-side pulley 41 in the direction of arrow A1, as shown in FIG. 7B. Actually, however, the dynamic slack 101 is absorbed in the resilient members 72 as soon as it occurs; there is no such a state as shown in FIGS. 7A-7D.

Figure 7C:
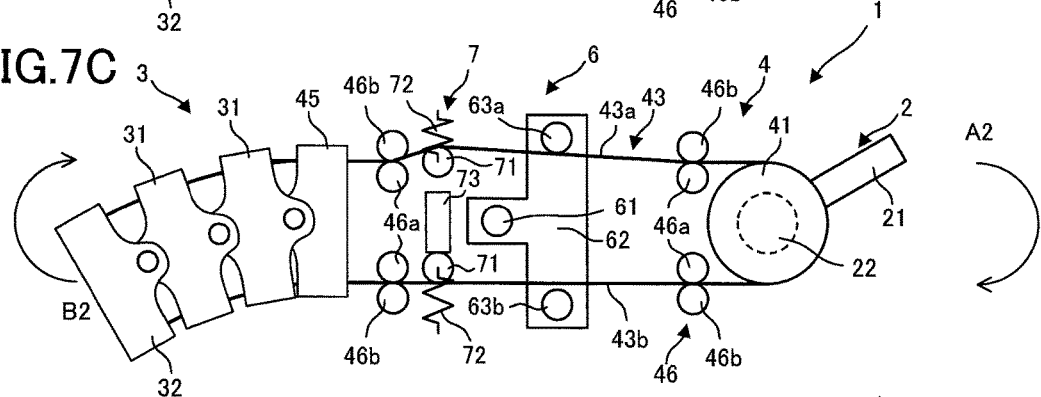

This in turn causes the tensile force of the first transmitting wire 43a to get small so that the idler pulleys 71 are pulled by the biasing force of the resilient members 72, as shown in FIG. 7C. As a result, the dynamic slack 101 is apparently absorbed.

Actually, however, as the handle 21 is rotated from the state shown in FIG. 7C in the direction of arrow A2 while the transmission compensating assembly 6 is not in action, it causes the tensile force of the first transmitting wire 43a to become greater than the biasing force of the resilient member 72. This then causes the first transmitting wire 43a to pull the idler pulleys 71 only resulting in elongation of the resilient members 72. In other words, the tensile force of the first transmitting wire 43a is not transmitted to the moving assembly 3 or the moving assembly 3 is not rotated.

Figure 7D:
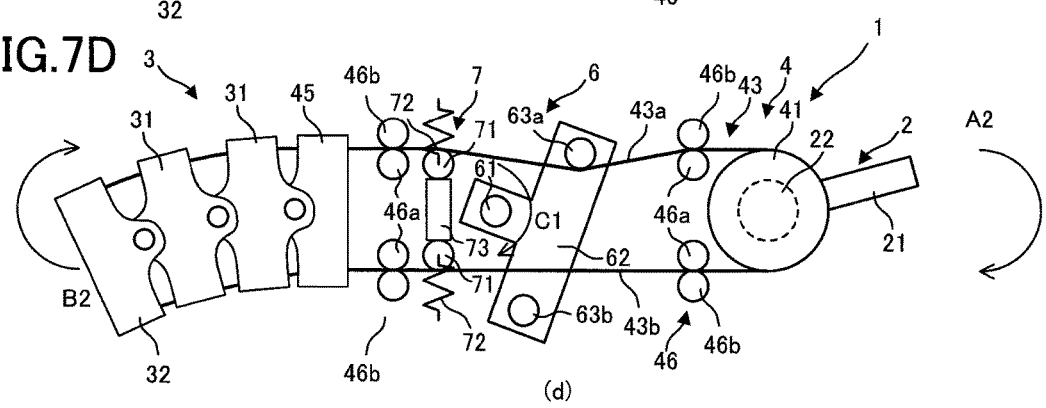

Therefore, the handle 21 is reversed from the direction of arrow A1 back to the direction of arrow A2 as shown in FIG. 7D, and when the first encoder 22 detects the reversal of the handle 21, the compensating motor 61 in the transmission compensating assembly 6 is driven to rotate the urging member 63 in the direction of arrow C1.

Referring to the fifth example of the manipulator 1, the urging member 63 rotates, as shown in FIG. 7D, allowing the first urging member 63a to urge the first transmitting wire 43a between the guide rollers 46, whereupon the idler pulleys 71 are pulled by the first transmitting wire 43a until they abut against the stopper 73. Thus, the transmitting wire 43 is urged in place by the first urging member 63a whereby the dynamic slack 101 in the transmitting wire 43 shown in FIG. 7B is rapidly removed.

Upon removal of the dynamic slack 101, the moving assembly 3 rotates in the direction of arrow B2 under the tensile force of the first transmitting wire 43a in association with the rotation of the handle 21.

According to the fifth example of the manipulator 1, it is thus possible to allow for rapid removal of the dynamic slack 101 in the transmitting wire 43 and rapid rotation of the moving assembly 3 in association with the rotation of the handle 21. It is also possible to allow for rapider rotation of the moving assembly 3 in association with the rotation of the handle 21 because the fifth example of the manipulator 1 may be configured such that the moving distance of the urging member 63 until the transmitting wire 43 is urged in place is shorter than that in the first to third examples.

As the dynamic slack 101 is temporarily absorbed in the resilient member 72, it allows for prevention of the transmitting wire 43 from deviating largely from the position of the neutral state by the dynamic slack 101. As a result, the urging member 63 urges the transmitting wire 43 in an unerring position so that there is no or little damage to the transmitting wire 43.

Figure 8A:
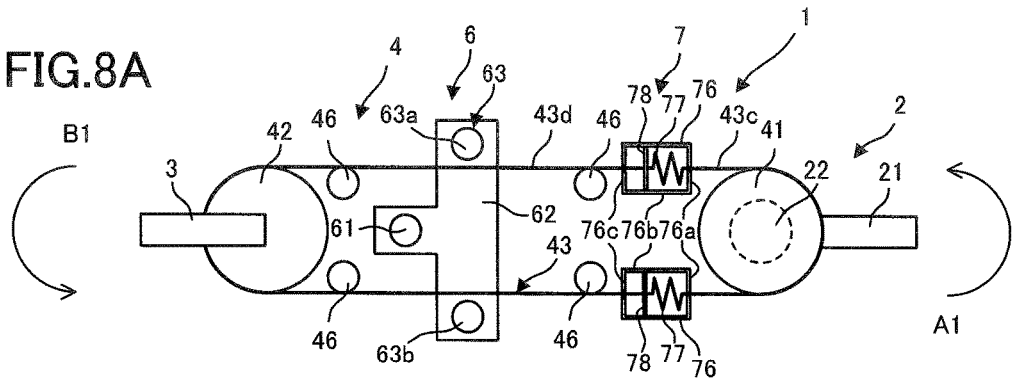
FIGS. 8A-8D are illustrative in schematic of the sixth example of the manipulator according to the first embodiment of the invention.
Figure 8B:
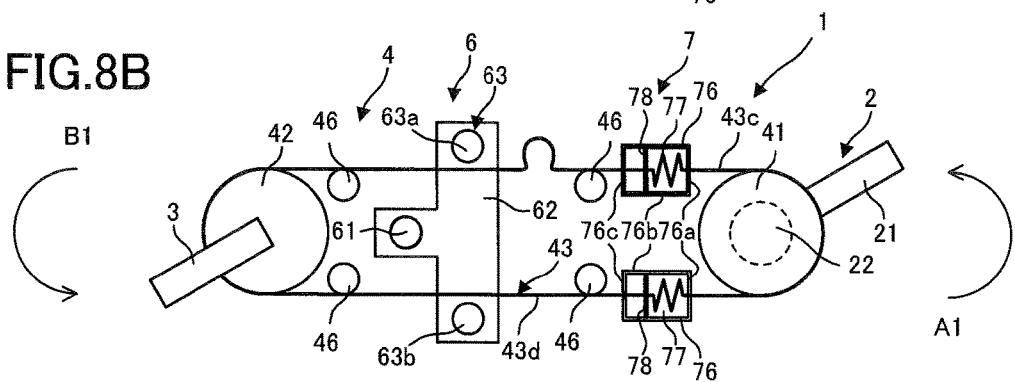
Figure 8C:
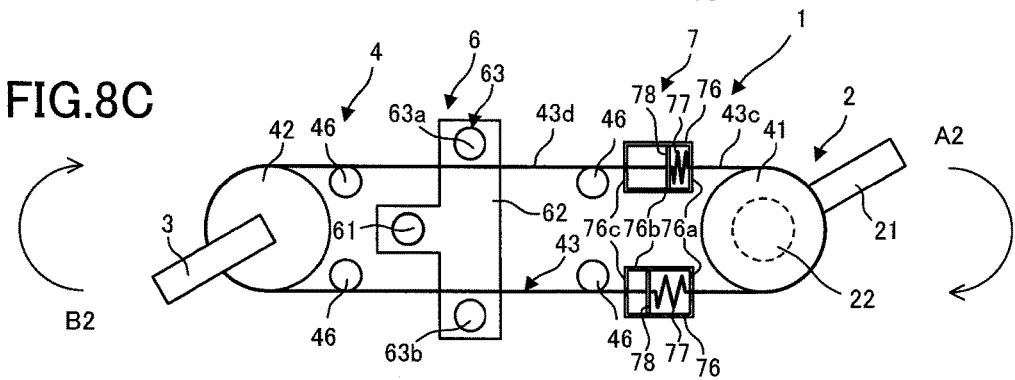
Figure 8D:
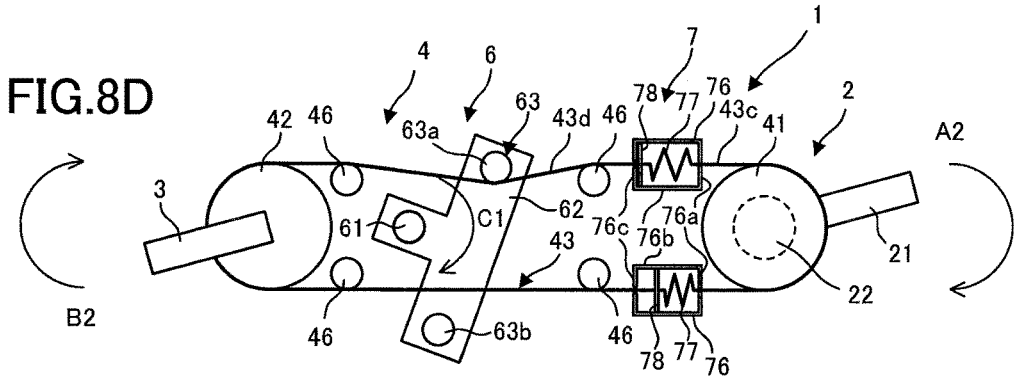
Figure 9A:
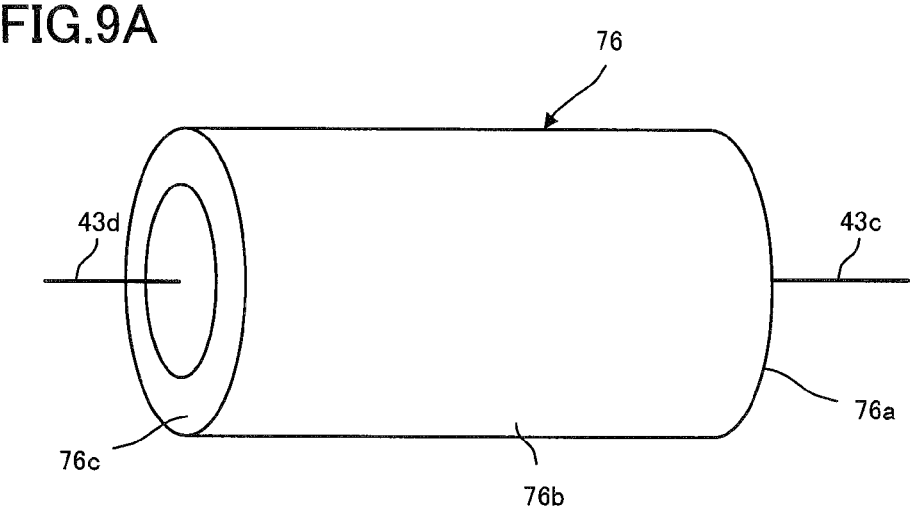
FIGS. 9A-9B are illustrative in schematic of a surplus absorber assembly in the sixth example of the manipulator according to the first embodiment of the invention.
Figure 9B:
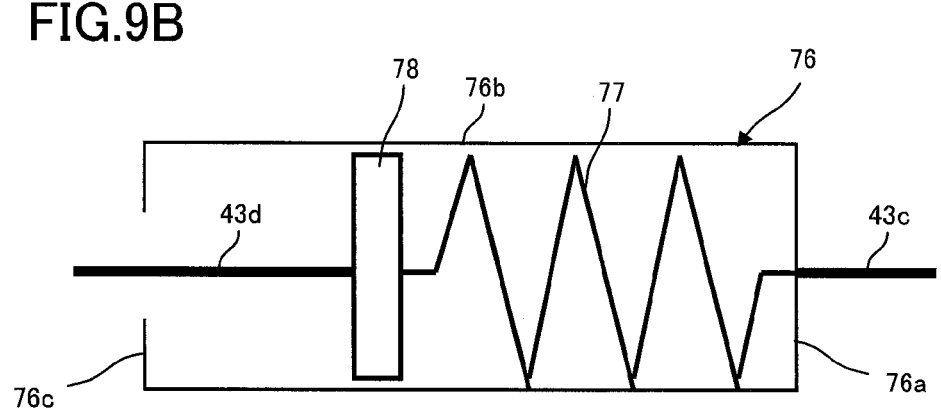

FIGS. 8A-8D are illustrative in schematic of the sixth example of the manipulator 1 according to the first embodiment described here, and FIGS. 9A-9B are illustrative in schematic of a surplus absorber assembly in the sixth example of the manipulator 1 according to the first embodiment described here.

Referring to the sixth example of the manipulator 1 shown in FIGS. 8A-8D, the fourth example of the manipulator 1 is additionally provided with a surplus absorber assembly 7. The rest of the manipulator 1 may be the same as explained with reference to the fourth example of FIGS. 6A-6C; so they will not explained any more.

The surplus absorber assembly 7 includes a first support member 76, a resilient member 77, and a second support member 78. The first support member 76 is attached to one end of an operating-side transmitting wire 43c routed around an operating-side pulley 41 to support one end of the resilient member 77. The second support member 78 is attached to one end of a moving-side transmitting wire 43d routed around a moving-side pulley 42 to support the other end of the resilient member 77.

A surplus absorber assembly 7 having a similar construction is also provided between the other end of the operating-side transmitting wire 43c and the other end of the moving-side transmitting wire 43d.

Referring to the sixth example of the manipulator 1, the first support member 76 comprises a boxy case including a bottom 76a having the operating-side transmitting wire 43c attached to it, a tubular portion 76b extending vertically from the bottom 76a and located in opposition to the operating-side transmitting wire 43c to surround the resilient member 77, and a lid 76c located in opposition to the bottom 76a with respect to the tubular portion 76b and provided with a bore through which the moving-side transmitting wire 43d is passed.

The resilient member 77 is attached at one end to the side of the bottom 76a of the first support member 76 opposite to the operating-side transmitting wire 43c and at the other end to the second support member 78, and surrounded with the tubular portion 76b. The second support member 78 is attached to the other end of the resilient member 77 on the bottom 76a side and to the moving-side transmitting wire 43d on the lid 76c side in such a way as to be movable into the first support member 76. Note here that the second support member 78 is larger than the bore formed through the lid 76c; so it cannot pass through that bore.

The sixth example of the manipulator 1 according to the first embodiment described herein is actuated as follows.

When an operator (not shown) rotates the handle 21 from a neutral state depicted in FIG. 8A in the direction of arrow A1 into a state of FIG. 8B, there is a dynamic slack 101 occurring in association with the rotation of the handle 21 and operating-side pulley 41 in the direction of arrow A1, as shown in FIG. 8B. Actually, however, the dynamic slack 101 is absorbed in the resilient members 77 as soon as it occurs; there is no such a state as shown in FIG. 8B.

This in turn causes the tensile force of the transmitting wire 43 to get small so that the second support member 78 is pulled by the biasing force of the resilient members 77. As a result, the dynamic slack 101 is apparently absorbed.

Actually, however, as the handle 21 is rotated from the state shown in FIG. 8C in the direction of arrow A2 while the transmission compensating assembly 6 is not in action, it causes the tensile force of the transmitting wire 43 to become greater than the biasing force of the resilient member 77. This then causes the operating-side transmitting wire 43d to pull the second support member 78, only resulting in elongation of the resilient members 77. In other words, the tensile force of the transmitting wire 43 is not transmitted to the moving pulley 42 or the moving assembly 3 is not rotated.

Therefore, the handle 21 is reversed from the direction of arrow A1 back to the direction of arrow A2 as shown in FIG. 8D, and when the first encoder 22 detects the reversal of the handle 21, the compensating motor 61 in the transmission compensating assembly 6 is driven to rotate the urging member 63 in the direction of arrow C1.

Referring to the sixth example of the manipulator 1, the urging member 63 rotates, as shown in FIG. 8D, allowing the first urging member 63a to urge the moving-side transmitting wire 43d between the guide rollers 46, whereupon the second support member 78 is pulled by the moving-side transmitting wire 43d until it abuts against the lid 76c of the first support member 76, and the first 76 and the second support member 78 move as an integral unit together with the transmitting wire 43. Thus, the transmitting wire 43 is urged in place by the first urging member 63a whereby the dynamic slack 101 in the transmitting wire 43 shown in FIG. 8B is rapidly removed.

Upon removal of the dynamic slack 101, the moving assembly 3 rotates in the direction of arrow B2 under the tensile force of the transmitting wire 43 in association with the rotation of the handle 21.

According to the sixth example of the manipulator 1, it is thus possible to allow for rapider removal of the dynamic slack 101 in the transmitting wire 43 and rapider rotation of the moving assembly 3 in association with the rotation of the handle 21. It is also possible to allow for rapider rotation of the moving assembly 3 in association with the rotation of the handle 21, because the sixth example of the manipulator 1 may be configured such that the moving distance of the urging member 63 until the transmitting wire 43 is urged in place is shorter than that in the first to third examples of the manipulator 1.

As the dynamic slack 101 is temporarily absorbed in the resilient member 77, it allows for prevention of the transmitting wire 43 from deviating largely from the position of the neutral state by the dynamic slack 101. As a result, the urging member 63 urges the transmitting wire 43 in an unerring position so that there is no or little damage to the transmitting wire 43 by the urging member 63.

Further, the first 76 and the second support member 78 move as an integral unit together with the transmitting wire 43 and there is no change in the orbit of the transmitting wire 43. This allows the urging member 63 to urge the transmitting wire 43 in a more unerring position so that damage to the transmitting wire 43 from the urging member 63 is much more reduced.

Figure 10A:
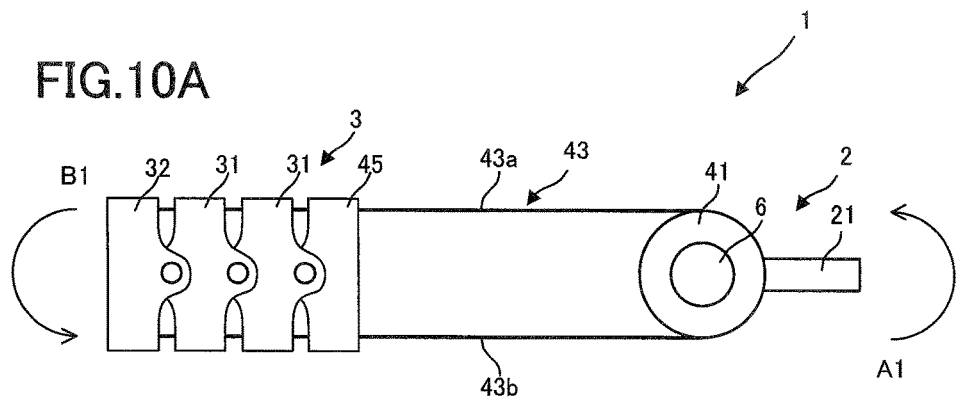
FIGS. 10A-10B are illustrative in schematic of the first example of the manipulator according to the second embodiment of the invention.
Figure 10B:
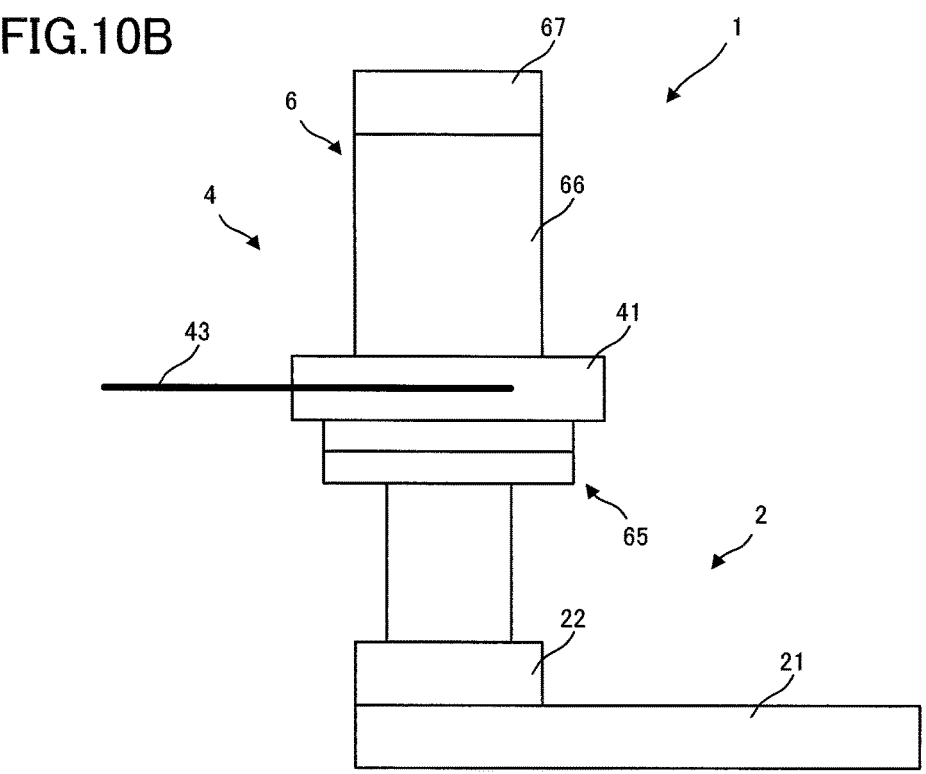

FIGS. 10A-10B are illustrative in schematic of the first example of the manipulator 1 according to the second embodiment of the invention.

Referring to the first example of the manipulator 1 according to the second embodiment shown in FIGS. 10A-10B, the operating assembly 2 and transmission compensating assembly 6 in the first example of the manipulator 1 according to the first embodiment described here are partly modified in construction. The rest of the manipulate 1 may be the same as explained with reference to FIG. 1; so they will not be explained any more.

In the manipulator 1 shown in FIGS. 10A-10B, the operating assembly 2 includes a handle 21, a first encoder 22, and a first clutch 65, and the transmission compensating assembly 6 in the manipulator 1 includes a compensating motor 66, and a second encoder 67.

The handle 21 provides an operating member, the first encoder 22 provides an operating state acquisition member, and the first clutch 65 provides an operating disengagement member. The compensating motor 66 provides a drive member while the second encoder 67 provides a driving state acquisition member.

While the motor is used as the drive member, it is to be understood that any desired actuator capable of producing driving force may be used. Likewise, the operating state acquisition device is not specifically limited to the encoder; so any desired device capable of obtaining the state of rotation of the operating assembly 2 may be used. For instance, an angle sensor or angular velocity sensor may be used. In addition, any desired device capable of obtaining the angle of rotation of the operating-side pulley 41 may also be used. Likewise, the driving state acquisition device is not specifically limited to the encoder, and any desired device capable of obtaining the state of rotation of the compensating motor 66 may be used. For instance, an angle sensor or angular velocity sensor may be used.

In the second embodiment described here, the handle 21 is schematically shown in the form of a rod-like member, but it may take the form of a multi-joint arm or a member having a shape suitable for operating a treatment tool or the like disposed on the moving assembly 3 such as the grips of scissors. The first encoder 22 detects an input value to the handle 21. The first clutch 65 is a member that is located between the handle 21 and the operating-side pulley 41 to cut off or disengage the transmission of force from the handle 21 to the operating-side pulley 41.

The compensating motor 66 rotates the operating-side pulley 41 for removal of the dynamic slack 101, and may rotate the operating-side pulley 41 to assist in the rotation of the handle 21 as well. The second encoder 67 detects the rotation of the compensating motor 66. The first clutch 65 is a member that disengages the transmission of force from the handle 21 to the operating-side pulley 41.

The first example of the manipulator 1 according to the second embodiment described here is actuated as follows.

FIGS. 11A-11B, 12A-12B and 13A-13B are each illustrative of the actuation of the manipulator 1 according to the second embodiment described here. Note here that the arrows in FIGS. 11A-11B, 12A-12B and 13A-13B are schematically indicative of clutch engagement/disengagement.

Figure 11A:
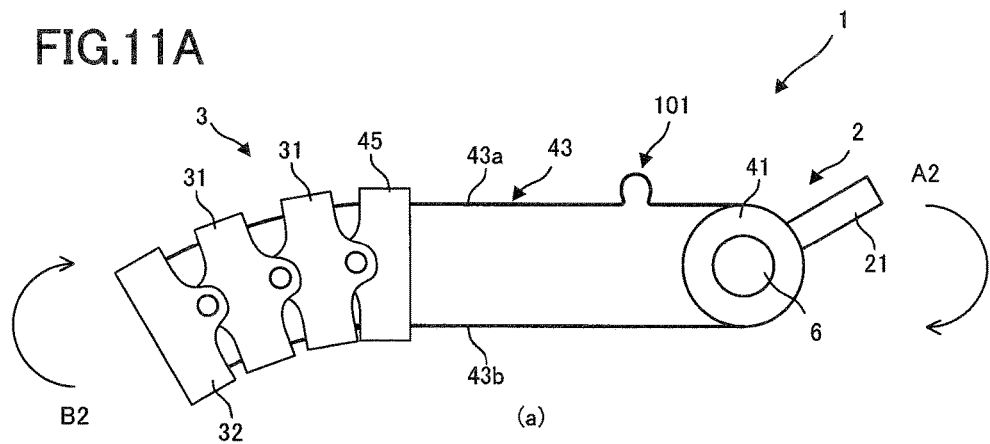
FIGS. 11A-11B are illustrative in schematic of the actuation of the first example of the manipulator according to the second embodiment of the invention.
Figure 11B:
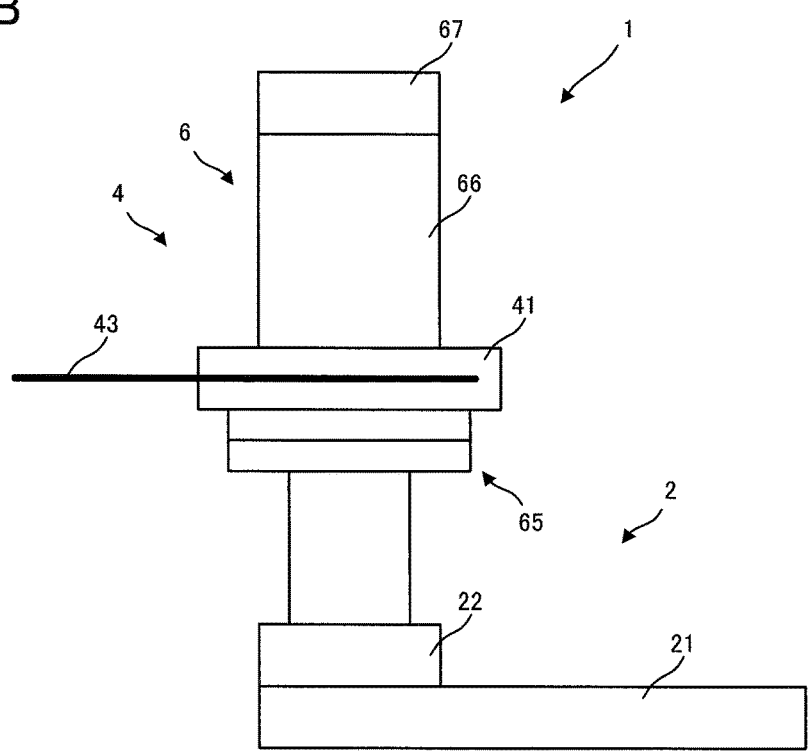

When an operator (not shown) operates the handle 21 from a neutral state shown in FIGS. 10A-10B in the direction of arrow A1 into a state shown in FIGS. 11A-11B, there is a dynamic slack 101 occurring in association with the rotation of the handle 21 and operating-side pulley 41 in the direction of arrow A1, as depicted in FIGS. 11A-11B.

Figure 12A:
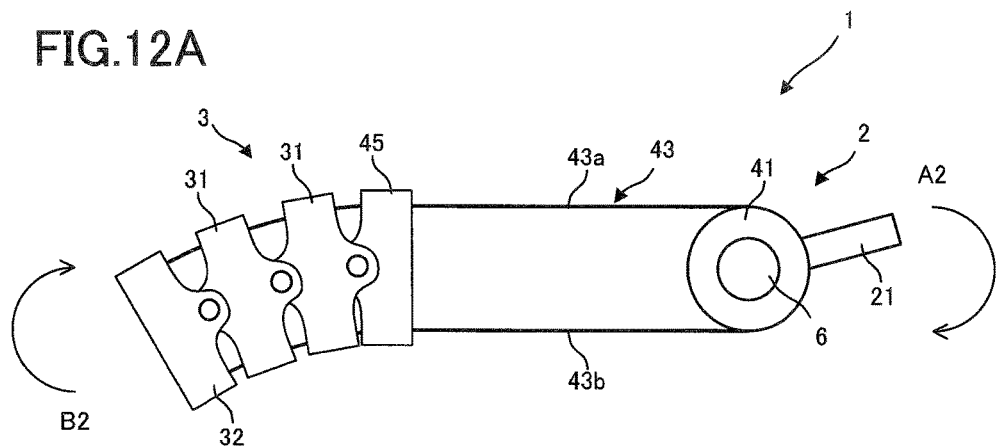
FIGS. 12A-12B are illustrative in schematic of the actuation of the first example of the manipulator according to the second embodiment of the invention.
Figure 12B:
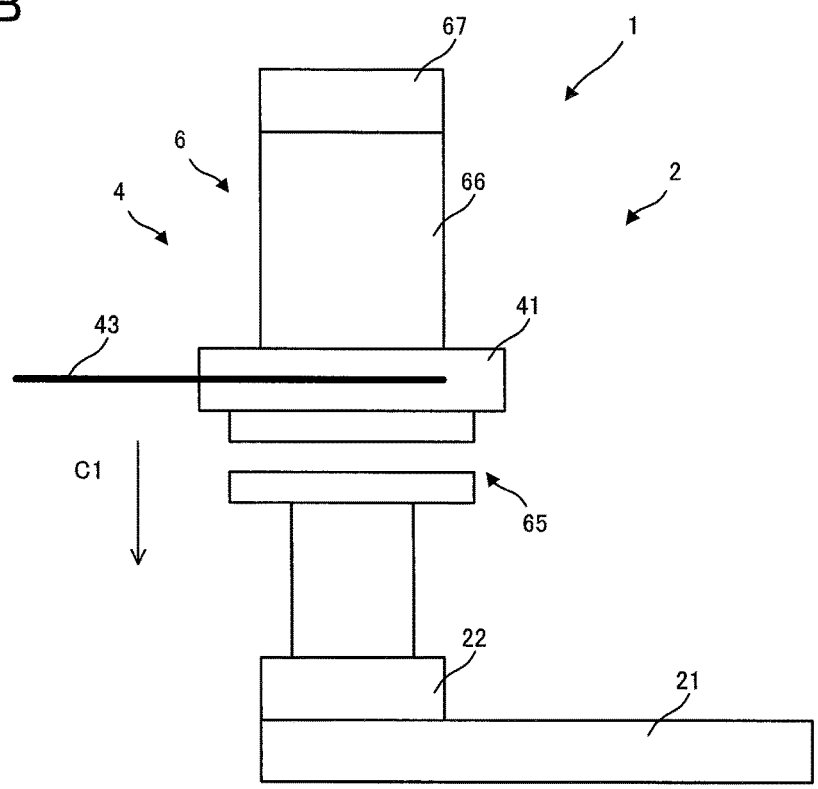

Upon subsequent reversal of the handle 21 back to the direction of arrow A2 as shown in FIGS. 11A-11B and 12A-12B, the first encoder 22 is actuated to detect the reversal of the handle 21. Upon detection of the reversal of the handle 21 by the first encoder 22, the first clutch 65 in the operating assembly 2 is disengaged in the direction of arrow C1 and the compensating motor 66 is driven as shown in FIGS. 12A-12B. As the compensating motor 66 is driven, it allows for rapid removal of the dynamic slack 101 in the transmitting wire 43, shown in FIGS. 11A-11B. Note here that in the state shown in FIGS. 12A-12B, even when the operating-side pulley 41 is rotated by the compensating motor 66, the driving force of the compensating motor 66 is not transmitted to the handle 21 because the first clutch 65 remains disengaged.

Figure 13A:
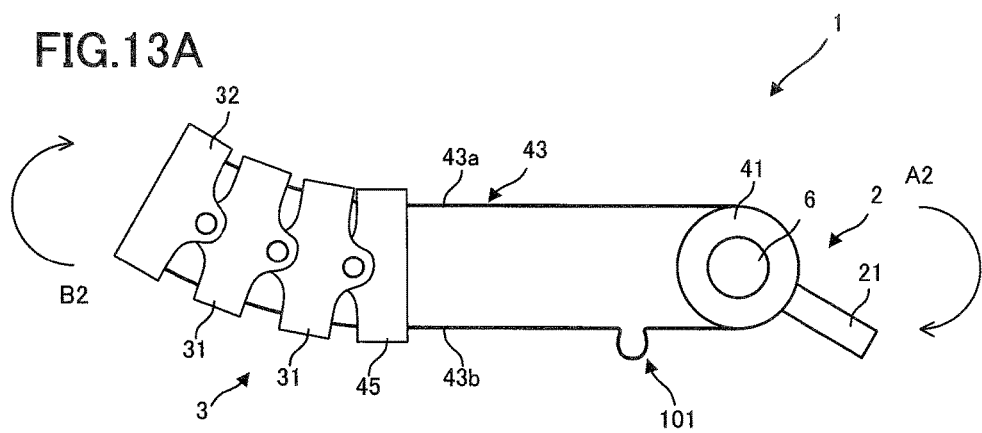
FIGS. 13A-13B are illustrative in schematic of the actuation of the first example of the manipulator according to the second embodiment of the invention.
Figure 13B:
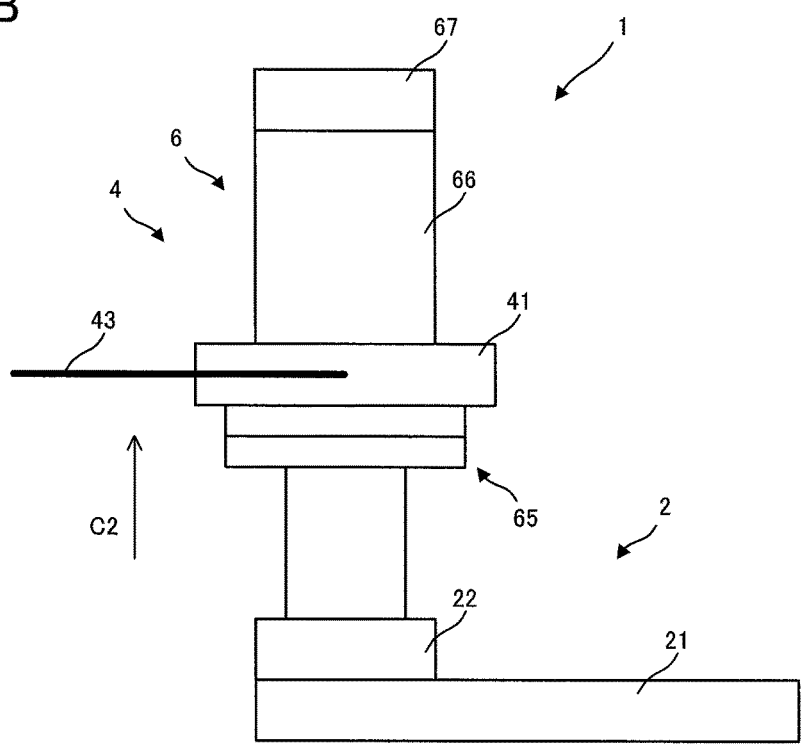

Following removal of the dynamic slack 101, the first clutch 65 is engaged in the direction of arrow C2 to rotate the moving assembly 3 in the direction of arrow B2 under the tensile force of the transmitting wire 43 resulting from the rotation of the handle 21, as shown in FIGS. 13A-13B. Then, the compensating motor 66 may be driven to assist in the operating force of the handle 21.

According to the first example of the manipulator 1 according to the second embodiment described here, it is thus possible to rapidly take the dynamic slack 101 out of the transmitting wire 43 and make sure rapid rotation of the moving assembly 3 in association with the rotation of the handle 21.

The first example of the manipulator 1 according to the second embodiment described here may be installed in a smaller footprint (space) without damage to the transmitting wire 43 as compared with the manipulator 1 according to the first embodiment, because of no need for providing any urging member for urging the transmitting wire 43 in place. In addition, the compensating motor 66 assists in the operating force of the handle 21 so much so that the manipulator can be operated with agility.

Figure 14A:
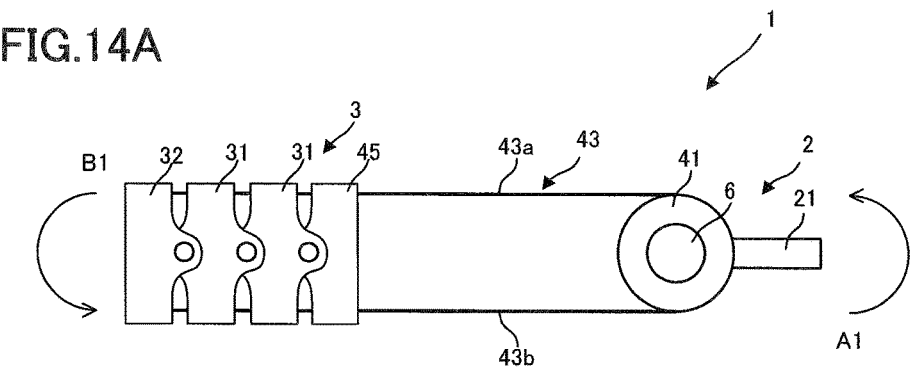
FIGS. 14A-14B are illustrative in schematic of the second example of the manipulator according to the second embodiment of the invention.
Figure 14B:
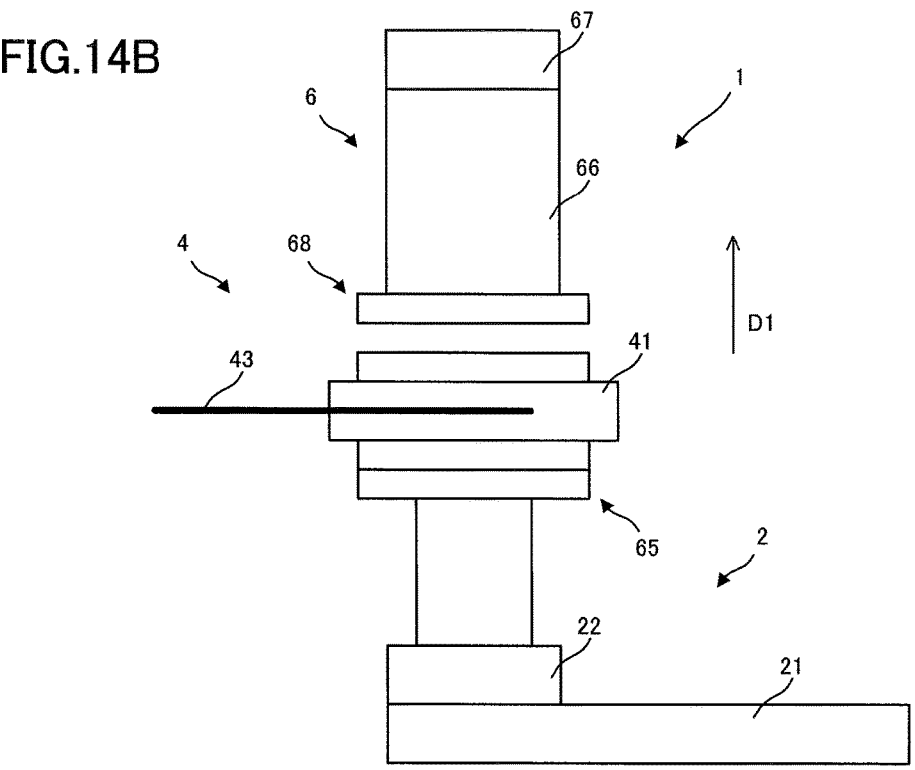

FIGS. 14A-14B are a schematic view of the second example of the manipulator 1 according to the second embodiment described here.

In the second example of the manipulator 1 according to the second embodiment shown in FIGS. 14A-14B, the transmission compensating assembly 6 in the first example of the manipulator 1 according to the second embodiment is partly modified in construction. The rest of the manipulator may be the same as explained with reference to FIGS. 10A-10B; so they will not be explained any more.

The transmission compensating assembly 6 in the manipulator 1 shown in FIGS. 14A-14B includes a second clutch 68.

The second clutch 68 is a member that disengages the transmission of force from the compensating motor 66 to the operating-side pulley 41.

The second example of the manipulator 1 according to the second embodiment described herein is actuated as follows.

Figure 15A:
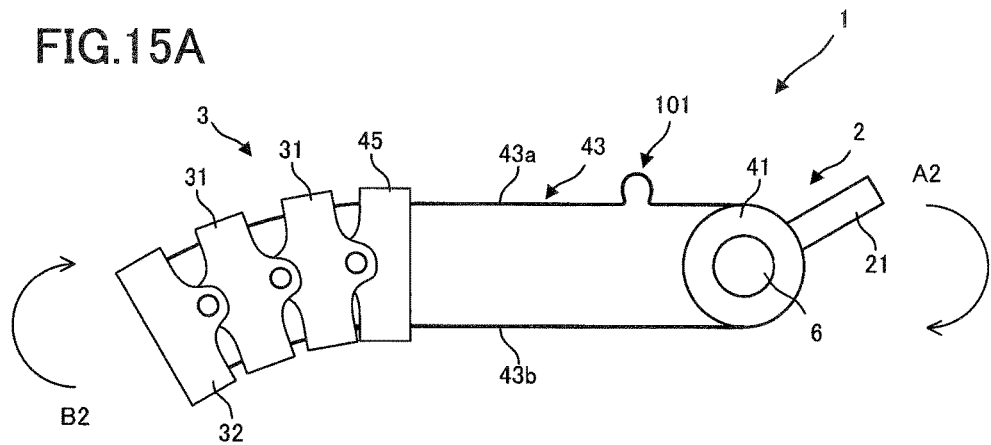
FIGS. 15A-15B are illustrative in schematic of the actuation of the second example of the manipulator according to the second embodiment of the invention.
Figure 15B:
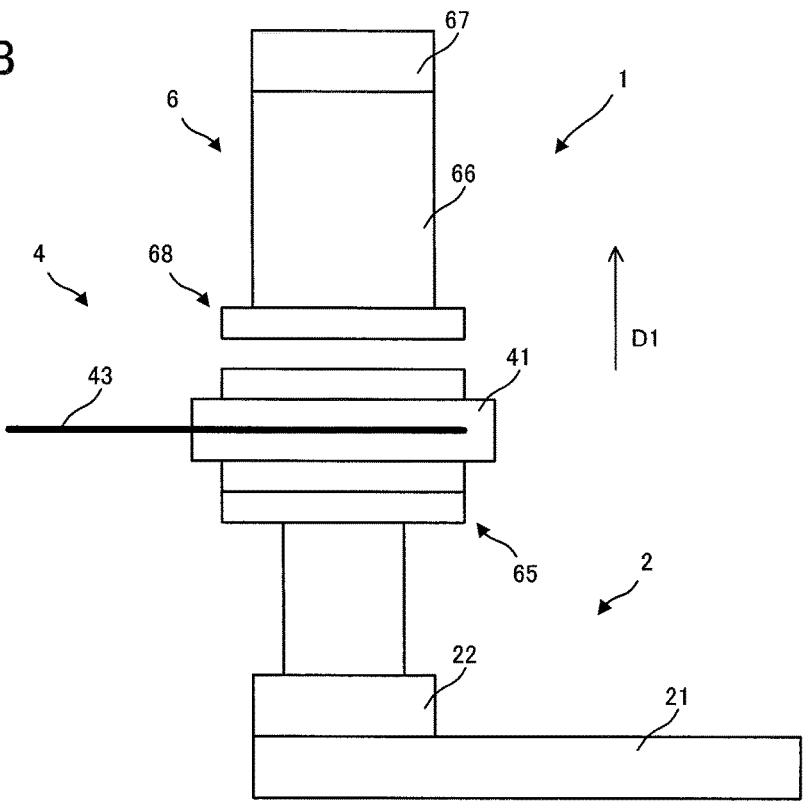

When an operator (not shown) operates the handle 21 from a neutral state shown in FIGS. 14A-14B in the direction of arrow A1 into a state shown in FIGS. 15A-15B, there is a dynamic slack 101 occurring in association with the rotation of the handle 21 and operating-side pulley 41 in the direction of arrow A1, as shown in FIGS. 15A-15B.

At this time the second clutch 68 remains still disengaged in the direction of an arrow D1 where the operating-side pulley 41 is rotated only by the operation of the handle 21.

Figure 16A:
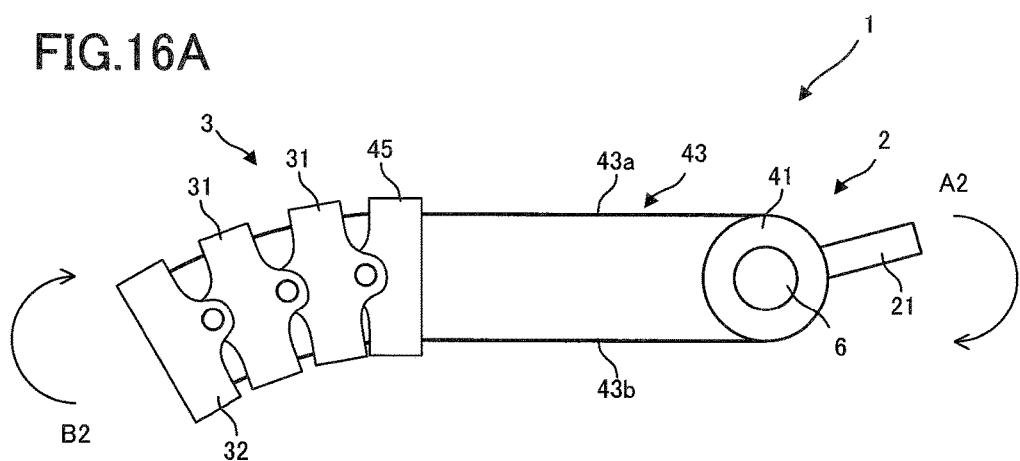
FIGS. 16A-16B are illustrative in schematic of the actuation of the second example of the manipulator according to the second embodiment of the invention.
Figure 16B:
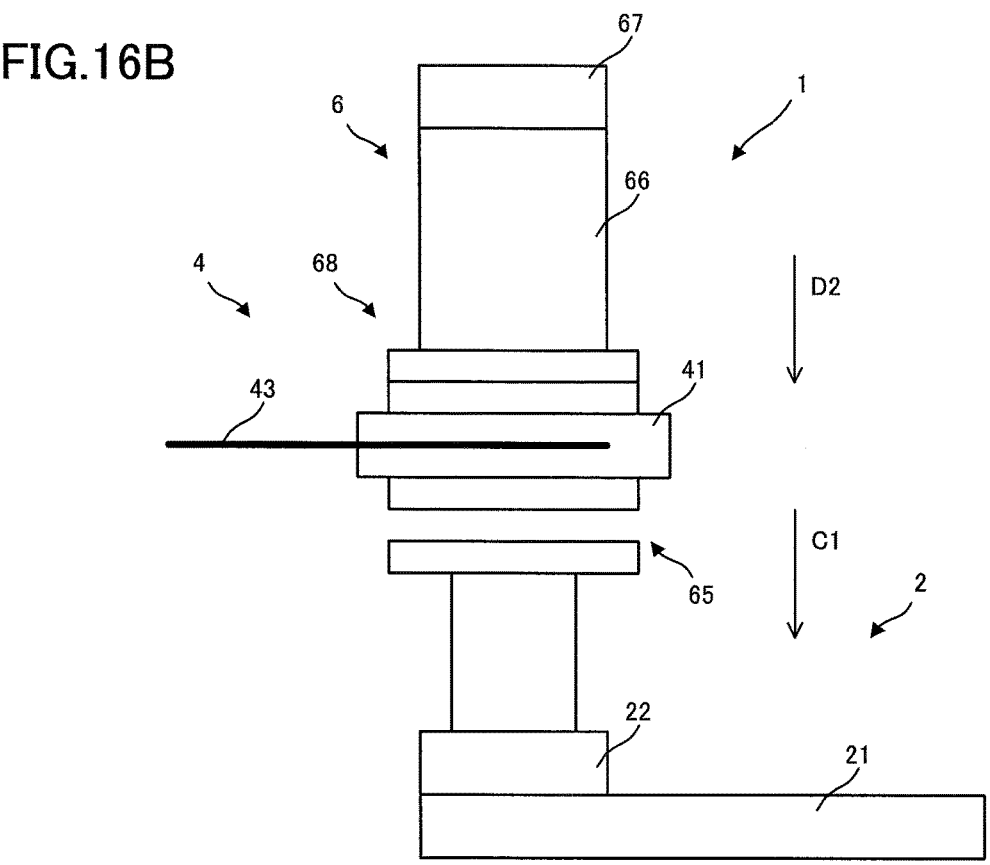

Subsequently, when the handle 21 is reversed back in the direction of arrow A2 as shown in FIGS. 15A-15B and 16A-16B, the first encoder 22 is actuated to detect the reversal of the handle 21. Upon detection of the reversal of the handle 21 by the first encoder 22, the first clutch 65 in the operating assembly 2 is disengaged in the direction of arrow C2, and the second clutch 68 in the transmission compensating assembly 6 is engaged in the direction of arrow D2 to drive the compensating motor 66 as shown in FIGS. 16A-16B. As the compensating motor 66 is driven, it allows for rapid removal of the dynamic slack 101 in the transmitting wire 43 shown in FIGS. 15A-15B. Note here that in the state shown in FIGS. 16A-16B, even when the operating-side pulley 41 is rotated by the compensating motor 66, the driving force of the compensating motor 66 is not transmitted to the handle 21 because the first clutch 65 remains disengaged.

Figure 17A:
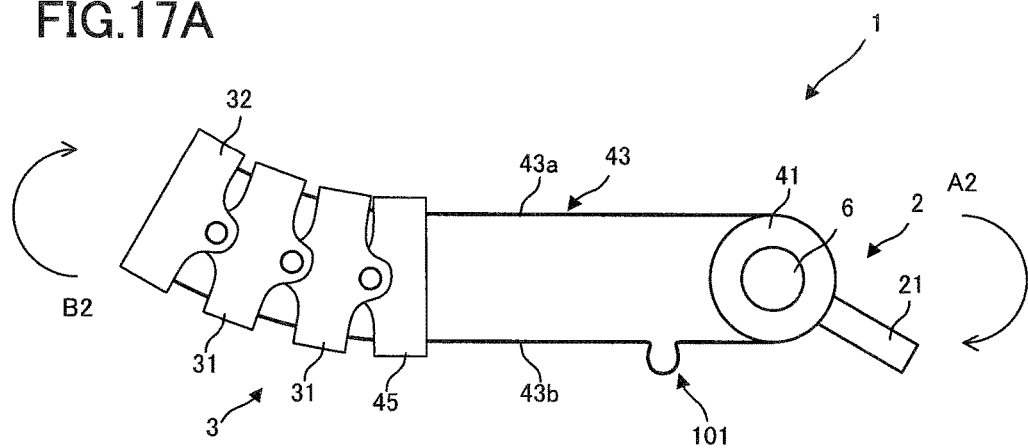
FIGS. 17A-17B are illustrative in schematic of the actuation of the second example of the manipulator according to the second embodiment of the invention.
Figure 17B:
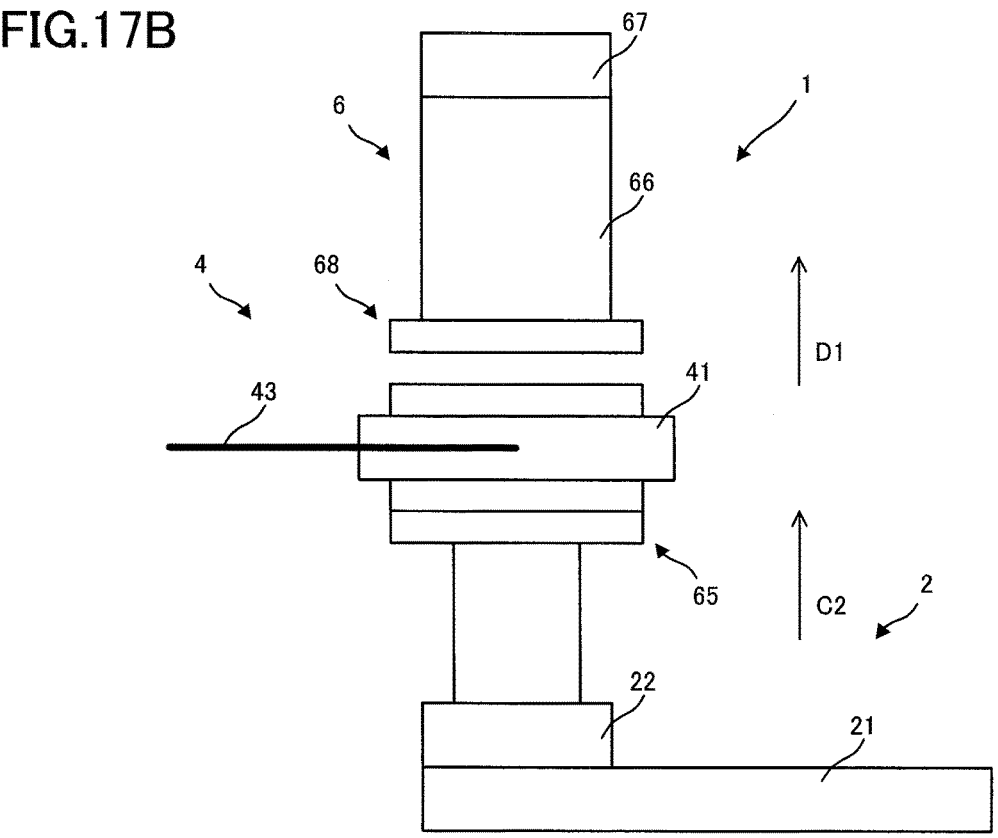

Following removal of the dynamic slack 101, the first clutch 65 is engaged in the direction of arrow C2 and the second clutch 68 is disengaged in the direction of arrow D1 to rotate the moving assembly 3 in the direction of arrow B2 under the tensile force of the transmitting wire 43 resulting from the rotation of the handle 21, as shown in FIGS. 17A-17B. Then, the compensating motor 66 may be driven to assist in the operating force of the handle 21.

According to the second example of the manipulator 1 according to the second embodiment described here, it is thus possible to rapidly take the dynamic slack 101 out of the transmitting wire 43 and make sure rapid rotation of the moving assembly 3 in association with the rotation of the handle 21.

The second example of the manipulator 1 according to the second embodiment described here may be installed in a smaller footprint (space) without damage to the transmitting wire 43 as compared with the manipulator 1 according to the first embodiment, because of no need for providing any urging member for urging the transmitting wire 43 in place.

Unlike the first example of the manipulator 1, the second example of the manipulator 1 according to the second embodiment includes the second clutch 68 capable of disengaging the transmission of force between the compensating motor 66 and the operating-side pulley 41 so that the operator can operate the handle 21 with agility and without feeling the weight of the compensating motor 66 acting as a sort of resistance.

Next, a surgery support system 10 is explained as one example of the manipulator system to which the manipulator 1 described here is applied.

Figure 18:
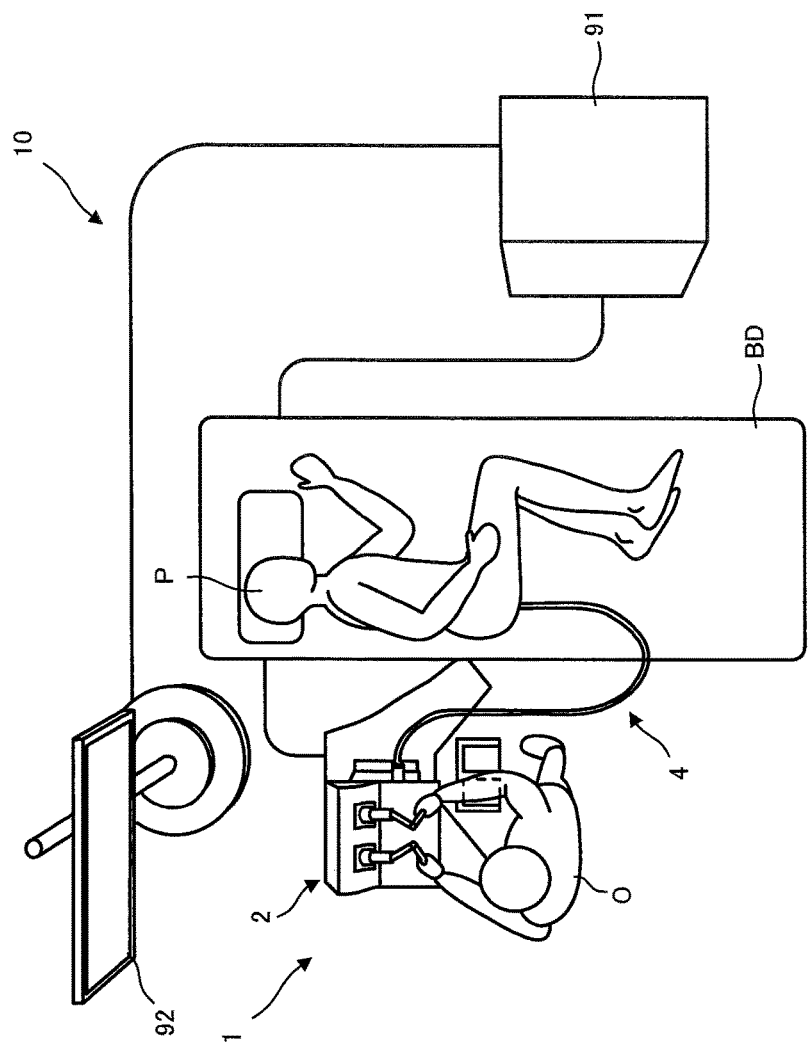
FIG. 18 shows on example of the manipulator system according to one embodiment of the invention.
Figure 19:
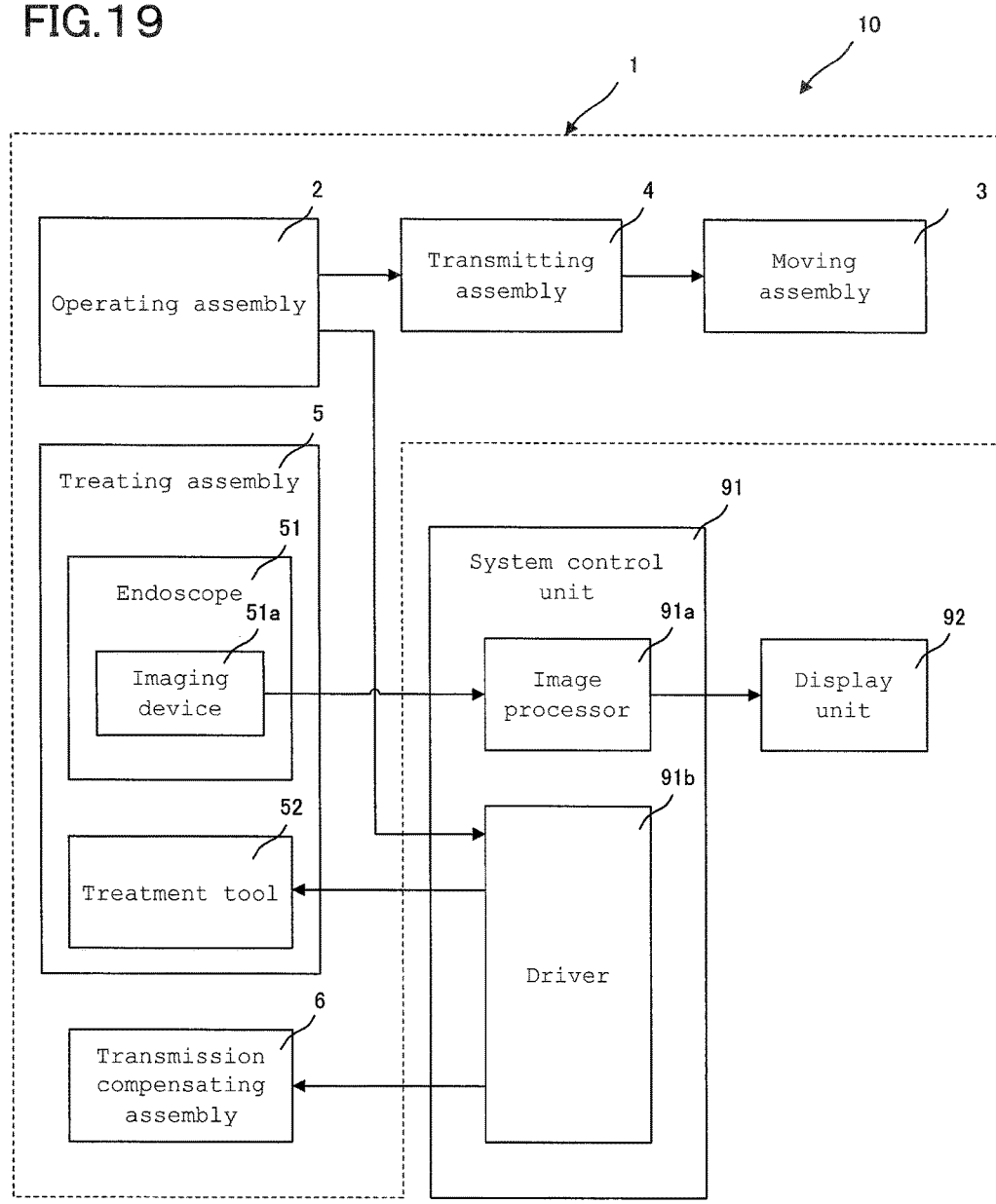
FIG. 19 is a block diagram for one example of the manipulator system according to one embodiment of the invention.
Figure 20A:
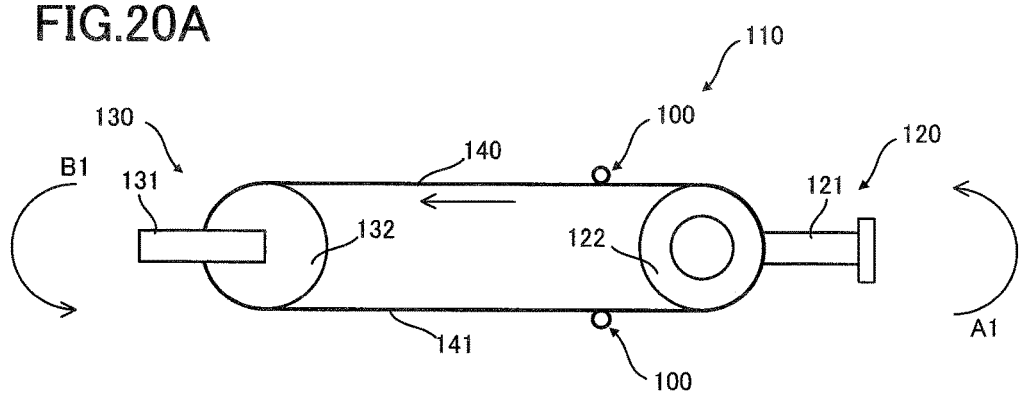
FIGS. 20A-20C are illustrative in schematic of the actuation of a conventional manipulator.
Figure 20B:
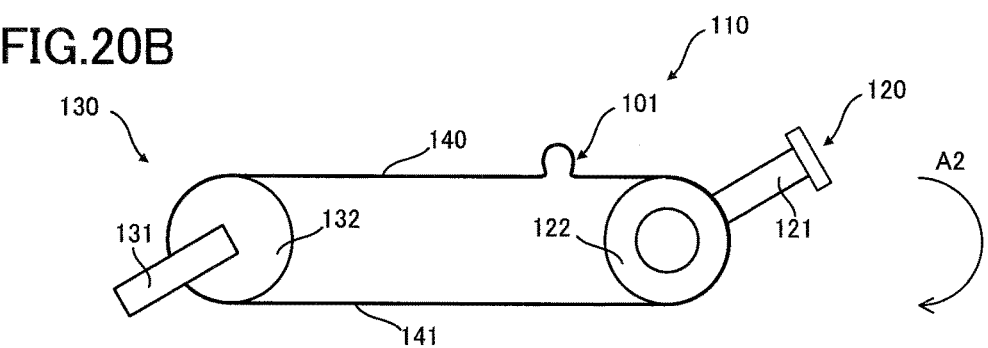
Figure 20C:
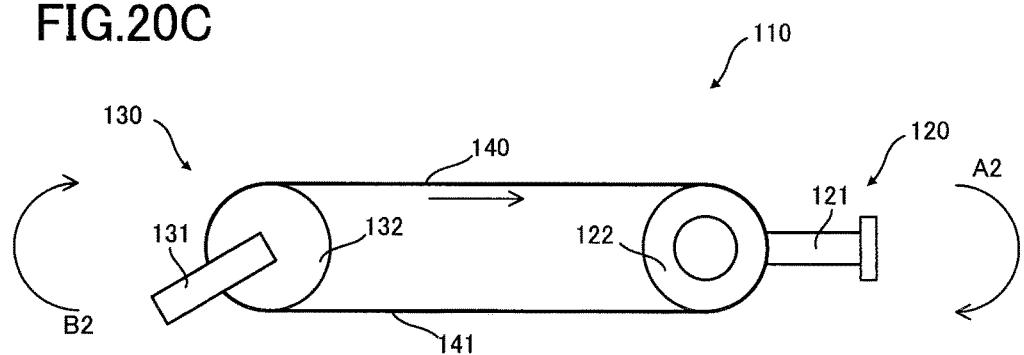

FIG. 18 shows the surgery support system 10 to which the manipulator 1 described here is applied, and FIG. 19 shows a typical system configuration of the surgery support system 10 to which the manipulator 1 described here is applied.

The manipulator 1 shown in FIG. 1 is applied to the surgery support system 10 described here. The surgery support system 10 comprises a manipulator 1, a control block or unit 91 for gaining control of the manipulator 1, and a display block or unit 92 for displaying images obtained through the manipulator 1, wherein the manipulator 1 includes an operating block or assembly 2 operated by an operator O, a moving block or assembly 3 of FIG. 1 capable of being inserted through the body of a patient P on an operating table BD, for instance, a limp internal organ such as the large intestine, a transmitting block or assembly 4 for transmitting an input from the operating block 2 to the moving block 3 and capable of being partly inserted into the internal organ, and a treatment block or assembly 5 of FIG. 1 including an endoscope or the like attached to the distal end of the moving block 3.

As showed FIG. 18, the operating assembly 2 includes a pair of operating handles attached to an operating table, a footswitch or the like located on a floor surface. The operating assembly 2 may have a multi-joint structure. The operating block 2 is mechanically connected to the transmitting block 4 and moving block 3 to bend the moving assembly 3. The angle of the operating assembly 2 in action is acquired from an angle acquisition device such as an encoder, and the control unit 91 uses the acquired signals to actuate a treatment tool 52 and a transmission compensating block or assembly 6 located at the distal end of the moving block 3 by way of a driver 91b.

In the rigid distal-end portion 32 of the moving assembly 3, the manipulator 1 includes an endoscope 51, a treatment tool 52 and so on in the form of the treatment assembly 5, as can be seen from FIG. 1. The endoscope 51 comprises a viewing optical system for obtaining in-vivo images, an imaging device 51a, a lighting optical system, and so on. An image obtained by the imaging device 51a via the viewing optical system is sent out to an image processor 91a in the control unit 91. The image processed at the image processor 91a is displayed on the display unit 92. Then, the operator O operates the manipulator 1 while viewing the images displayed on the display unit 92.

According to such surgery support system 10, it is possible to display unerring images asked for by the operator.

The manipulator 1 according to the embodiment described here comprises the operating assembly 2 operated by the operator, the moving assembly 3 operated through the operating assembly 2, the transmitting assembly 4 that couples the operating assembly 2 to the moving assembly 3 to transmit the driving force of the operating assembly 2 to the moving assembly 3, and the transmission compensating assembly 6 for compensating a dynamic surplus occurring in the transmitting assembly 4 in association with the operation of the operating assembly 2. It is thus possible to remove such dynamic surplus rapidly and permit the moving assembly 3 to move rapidly in association with the actuation of the operating assembly 2.

In the manipulator 1 according to the embodiment described here, the transmitting assembly 4 includes the operating-side pulley 41 that rotates together with the operating assembly 2, and the transmitting wire 43 that is at least partly routed around the operating-side pulley 41, and the transmission compensating assembly 6 makes up for a dynamic slack occurring in the transmitting wire 43 in association with the operation of the operating assembly 2. Thus, such dynamic slack can rapidly be removed and the moving assembly 3 can move rapidly in association with the operation of the operating assembly 2.

In the manipulator 1 according to the embodiment described here, the transmission compensating assembly 6 has a simple configuration including the urging member 63 for urging the transmitting wire 43 in place and a driving member 61 for driving the urging member 63 in association with the operation of the operating assembly 2. Through such a simple configuration it is thus possible to provide rapid removal of a dynamic slack and let the moving assembly 3 move rapidly in association with the operation of the operating assembly 2.

The manipulator 1 according to the embodiment described here includes the decelerator 24 for decelerating rotations entered from the operating pulley 41 into the operating assembly 2. It is thus possible to minimize the transmission of counteraction applied by the urging member 63 on the transmitting wire 43 from the operating-side pulley 41 to the operating assembly 2.

In the manipulator 1 according to the embodiment described here, the urging member 63 is capable of rotation and movement. Through a simple configuration it is thus possible to urge the urging member 63 onto the transmitting wire 43.

In the manipulator 1 according to the embodiment described here, the urging member 63 moves linearly so that it does no or little damage to the transmitting wire 43 and can unerringly be urged onto the transmitting wire 43.

In the manipulator 1 according to the embodiment described here, there are a plurality of urging members 63 provided in place so that the distance until the urging member 63 urges the transmitting wire 43 is shortened. It is thus possible to provide rapider removal of a dynamic slack and let the moving assembly 3 move more rapidly in association with the operation of the operating assembly 2.

The manipulator 1 according to the embodiment described here includes the guide rollers 46 disposed on both sides of a position where the transmitting wire 43 is urged by the urging member 63 in place. It is thus possible to urge the urging member 63 against the transmitting wire 43 in a more unerring position.

The manipulator 1 according to the embodiment described herein includes the idler pulley 71 in abutment with the transmitting wire 43, the resilient member 72 for biasing the idler pulley 71 on the transmitting wire 43 side, and the stopper 73 located in opposition to the resilient member 72 with respect to the idler pulley 71 to constrain movement of the idler pulley 71, and further includes the surplus absorber 7 for absorbing a dynamic slack occurring in the transmitting wire 43 in association with the action of the operating assembly 2. It is thus possible to prevent the transmitting wire 43 from deviating largely from the position of its neutral state due to the dynamic slack 101. This in turn permits the urging member 63 to urge the transmitting wire 43 in an unerring position thereby reducing damage caused by the urging member 63 to the transmitting wire 43.

In the manipulator 1 according to the embodiment described herein, the transmitting assembly 4 includes the moving-side pulley 42 that rotates together with the moving assembly 3, and the transmitting wire 43 is divided into the operating-side transmitting wire 43c routed around the operating-side pulley 41 and the moving-side transmitting wire 43d routed around the moving-side pulley 42, including the first support member 76 attached to one end and the other end of the operating transmission wire 43c, the second support member 78 attached to one end and the other end of the moving transmission wire 43d, and the resilient member 77 supported at one end by the first support member 76 and at the other end by the second support member 78 and further comprising the surplus absorber 7 for absorbing a dynamic slack occurring in the transmitting wire 43 in association with the operation of the operating assembly 2. It is thus possible to prevent the transmitting wire 43 from deviating largely from the position of its neutral state due to the dynamic slack 101. This in turn permits the urging member 63 to urge the transmitting wire 43 in an unerring position thereby reducing damage caused by the urging member 63 to the transmitting wire 43.

In the manipulator 1 according to the embodiment described herein, the first support member 76 includes a bottom 76a having the operating-side transmitting wire 43c attached to it, a tubular portion 76b extending vertically from the bottom 76a and located in opposition to the operating-side transmitting wire 43c to surround the resilient member 77, and a lid 76c located in opposition to the bottom 76a with respect to the tubular portion 76b and provided with a bore through which the moving-side transmitting wire 43d is passed. The resilient member 77 is attached at one end to the side of the bottom 76a of the first support member 76 opposite to the operating-side transmitting wire 43c and at the other end to the second support member 78, and surrounded with the tubular portion 76b. The second support member 78 is attached to the other end of the resilient member 77 on the bottom 76a side and to the moving-side transmitting wire 43d on the lid 76c side in such a way as to be movable into the first support member 76. This enables the first 76 and the second support member 78 to move as a unit together with the transmitting wire 43 with no change in the orbit of the transmitting wire 43. It is thus possible for the urging member 63 to urge the transmitting wire 43 in a more unerring position and minimize damage caused by the urging member 63 to the transmitting wire 43.

In the manipulator 1 according to the embodiment described herein, the transmission compensating assembly 6 includes the first clutch 65 for disengaging the transmission of force from the operating assembly 2 to the operating-side pulley 41, and further includes the driving member 66 for rotating the operating-side pulley 41 when the operating assembly 2 is disconnected from the operating-side pulley 41 by the first clutch 65. It is thus possible to provide rapid removal of the dynamic slack 101 and permit for rapid movement of the moving assembly 3 in association with the operation of the operating assembly 2. It is also possible to prevent transmission of rotation of the operating-side pulley 41 by the driving member 66 from the operating-side pulley 41 to the operating assembly 2.

In the manipulator 1 according to the embodiment described herein, the transmission compensating assembly 7 includes the second clutch 68 for cutting off the transmission of force from the drive member 66 to the operating-side pulley 41 such that when the operating assembly 2 is in action, the driving member 66 is disconnected from the operating-side pulley 41 by the second clutch 68. It is thus possible for the operator to operate the handle with agility and without feeling the weight of the compensating motor 6 acting as a sort of resistance.

The manipulator system 10 according to the embodiment described here comprises the manipulator 1, the control unit 91 for gaining control of the manipulator 1, and the display unit 92 for displaying images obtained through the manipulator 1. The manipulator 1 includes the endoscope 51 having the viewing optical system, imaging device and lighting optical system, and the control unit 91 controls the display unit 92 such that the images obtained through the endoscope 51 are displayed on it. It is thus possible to move the moving assembly 3 in a rapid way thereby displaying unerring images asked for by the operator.

It is to be understood that the invention is in no sense limited to the embodiments described herein. Explanations of the embodiments include a number of exemplary specifics; however, it would be obvious to those skilled in the art that variations or modifications added to them are encompassed in the scope of the invention. Thus, exemplary embodiments of the invention are herein disclosed without ridding the claimed invention of any generality and imposing any limitation thereon.

EXPLANATIONS OF THE REFERENCE NUMERALS

1: Manipulator
2: Operating assembly
21: Handle
22: First encoder (device for acquiring operating states)
23: Torque generator
24: Decelerator
3: Moving assembly
31: Bending tops
32: Rigid distal-end portion
33: Moving wire
4: Transmitting assembly
41: Operating-side pulley
42: Moving-side pulley
43: Transmitting wire
44: Flexible portion
45: Transition portion
46: Guide rollers
5: Treatment assembly
51: Endoscope
52: Treatment tool
6: Transmission compensating assembly
61: Compensating motor (driving member)
62: Moving member
63: Urging member
65: First clutch (operating-side disengagement member)
66: Compensating motor (driving member)
67: Second encoder (device for acquiring driving states)
68: Second clutch (driving-side disengagement member)
7: Surplus absorber assembly
71: Idler pulley
72: Resilient member
73: Stopper
76: First support member
77: Resilient member
78: Second support member
10: Surgery support system
91: Control unit
92: Display unit

What is claimed is:

1. A manipulator, comprising:
an operating assembly operated by an operator;
a moving assembly operated by the operating assembly;
a transmitting assembly including an operating-side pulley that rotates in association with operation of the operating assembly and a transmitting wire that is at least partly wound around the operating-side pulley to transmit power to the moving assembly,
a transmission compensating assembly including an urging member configured to urge against the transmitting wire, a moving member for moving the urging member against the transmitting wire, and a driving member for driving the moving member, wherein the transmission compensating assembly at least partially removes a slack in the transmitting wire by means of the urging member being urged against the transmitting wire;
a sensor for detecting a rotation of the operating assembly resulting from a rotational operation of the operating assembly; and
a controller configured to:
detect the rotation of the operating side-pulley in a given direction with respect to a rotating axis of the operating assembly; and
where the rotation is detected, drive the driving member to urge the urging member located between the moving assembly and the operating-side pulley against the transmitting wire for removal of the slack in the transmitting wire.

2. A manipulator as recited in claim 1, the transmitting wire includes a first wire and a second wire located between the moving assembly and the operating-side pulley, and the transmission compensating assembly makes up for the slack in only one of the first wire and the second wire.

3. A manipulator as recited in claim 2, wherein:
the transmission compensating assembly includes an operating-side disengagement member for disengaging transmission of force from the operating assembly to the operating-side pulley, and further includes a driving member for rotating the operating-side pulley when the operating assembly is disconnected from the operating-side pulley by the operating-side disengagement member.

4. A manipulator as recited in claim 3, wherein the transmission compensating assembly includes a moving-side disengagement member for disengaging transmission of force from the driving member to the operating-side pulley such that upon operation of the operating assembly, the driving member is disconnected from the operating-side pulley by the moving-side disengagement member.

5. A manipulator as recited in claim 1, wherein
the transmitting wire includes a first wire and a second wire located between the moving assembly and the operating-side pulley and the urging member is located between the first wire and the second wire to urge only one of the first wire and the second wire.

6. A manipulator as recited in claim 5, wherein the urging member rotates and moves.

7. A manipulator as recited in claim 5, wherein the urging member moves linearly.

8. A manipulator as recited in claim 5, wherein there are a plurality of the urging members provided.

9. A manipulator as recited in claim 5, wherein the transmitting wire includes guide rollers located on both sides of a position where the transmitting wire is urged by the urging member in place.

10. A manipulator as recited in claim 9, which includes:
an idler pulley in abutment on the transmitting wire;
a resilient member that biases the idler pulley on the transmitting wire side;
a stopper that is located with the idler pulley interposed between the stopper and the resilient member to constrain movement of the idler pulley; and
a surplus absorber assembly for absorbing a dynamic slack occurring in the transmitting wire in association with operation of the operating assembly.

11. A manipulator as recited in claim 9, wherein:
the transmitting assembly includes a moving-side pulley that rotates together with the moving assembly;
the transmitting wire is divided into an operating-side transmitting wire routed around the operating-side pulley and a moving-side transmitting wire routed around the moving-side pulley, and includes a first support member attached to one end and the other end of the operating-side transmitting wire, respectively, a second support member attached to one end and the other end of the moving-side transmission wire, respectively, and a resilient member supported at one end on the first support member and at the other end on the second support member, and further comprises a surplus absorber assembly capable of absorbing a dynamic slack occurring in the transmitting wire in association with operation of the operating assembly.

12. A manipulator as recited in claim 11, wherein:
the first support member includes a bottom to which the operating-side transmitting wire is attached, a tubular portion extending vertically from the bottom and located in opposition to the operating-side transmitting wire to surround the resilient member, and a lid located in opposition to the bottom with respect to the tubular portion and provided with a bore through which the moving-side transmission wire passes;
the resilient member attached at one end to a portion of the first support member in opposition to the operating-side transmitting wire on the bottom and at the other end to the second support member; and
the second support member is larger than the bore formed in the lid, and attached on the bottom side to the other end of the resilient member and on the lid side to the moving-side transmitting wire in such a way as to be movable in the first support member.

13. A manipulator system, comprising:
a manipulator as recited in claim 1,
a display unit for displaying images obtained through the manipulator; and
wherein the manipulator includes an endoscope having a viewing optical system, an imaging device and a lighting optical system, and
the controller further enables images obtained through the endoscope to be displayed on the display unit.

14. A manipulator as recited in claim 1, wherein the sensor is an encoder.

15. A manipulator as recited in claim 1, wherein the urging member is disposed between the operating-side pulley and the moving assembly.

16. A manipulator, comprising:
an operating assembly operated by an operator;
a moving assembly operated by the operating assembly;
a transmitting assembly including an operating-side pulley that rotates in association with operation of the operating assembly and a transmitting wire that is at least partly wound around the operating-side pulley to transmit power to the moving assembly, a transmission compensating assembly including an urging member configured to urge the transmitting wire, a moving member for moving the urging member, and a driving member for driving the moving member, wherein the transmission compensating assembly at least partially removes a slack in the transmitting wire by means of the urging member;

a sensor for detecting a rotation of the operating assembly resulting from a rotational operation of the operating assembly; and a controller configured to:
- detect the rotation of the operating side-pulley in a given direction with respect to a rotating axis of the operating assembly; and
- where the rotation is detected, drive the driving member to urge the urging member located between the moving assembly and the operating-side pulley against the transmitting wire for removal of the slack in the transmitting wire wherein the urging member is disposed between the moving assembly and the operating-side pulley.

17. A manipulator as recited in claim 16, wherein the sensor is an encoder.

* * * * *